US010632312B2

(12) United States Patent
Ziv

(10) Patent No.: US 10,632,312 B2
(45) Date of Patent: Apr. 28, 2020

(54) MONITORING AND STIMULATION MODULE

(71) Applicant: ZIV HEALTHCARE LTD., Rehovot (IL)

(72) Inventor: Amos Ziv, Rehovot (IL)

(73) Assignee: ZIV HEALTHCARE LTD., Rehovot (IL)

( * ) Notice: Subject to any disclaimer, the term of this patent is extended or adjusted under 35 U.S.C. 154(b) by 42 days.

(21) Appl. No.: 15/761,624

(22) PCT Filed: Sep. 20, 2016

(86) PCT No.: PCT/IL2016/051036
§ 371 (c)(1),
(2) Date: Mar. 20, 2018

(87) PCT Pub. No.: WO2017/051408
PCT Pub. Date: Mar. 30, 2017

(65) Prior Publication Data

US 2019/0001131 A1 Jan. 3, 2019

Related U.S. Application Data

(60) Provisional application No. 62/221,152, filed on Sep. 21, 2015.

(51) Int. Cl.
*A61B 5/00* (2006.01)
*A61N 1/362* (2006.01)
(Continued)

(52) U.S. Cl.
CPC .......... *A61N 1/3625* (2013.01); *A61B 5/0245* (2013.01); *A61B 5/02405* (2013.01);
(Continued)

(58) Field of Classification Search
CPC ............ A61B 5/02405; A61B 5/02438; A61B 5/0245; A61B 5/0404; A61B 5/4836;
(Continued)

(56) References Cited

U.S. PATENT DOCUMENTS 4,120,294 A 10/1978 Wolfe
4,221,223 A 9/1980 Linden
(Continued)

FOREIGN PATENT DOCUMENTS

EP 1690565 A2 8/2006
EP 2540221 A1 1/2013
(Continued)

OTHER PUBLICATIONS

Marek Malik, "Heart rate variability, Standards of Measurement, Physiological Interpretation, and Clinical Use", European Heart Journal (1996) 17, 354-381.
(Continued)

*Primary Examiner* — George Manuel
(74) *Attorney, Agent, or Firm* — The Roy Gross Law Firm, LLC; Roy Gross

(57) ABSTRACT

Disclosed herein are portable and integrated modules and devices for non-intrusive neuromodulation and monitoring of heart function, and methods of operation thereof. The modules and devices include a monitoring unit, an electrical stimulation inducing unit, and three electrodes, such that one of the electrodes is dual-function, being controllably utilized for neuromodulation or for monitoring of heart function.

21 Claims, 14 Drawing Sheets

(51) Int. Cl.

| | |
|---|---|
| ***A61B 5/0404*** | (2006.01) |
| ***A61N 1/36*** | (2006.01) |
| ***A61B 5/0245*** | (2006.01) |
| ***A61B 5/024*** | (2006.01) |
| ***A61N 1/04*** | (2006.01) |
| ***A61N 1/365*** | (2006.01) |

(52) U.S. Cl.

CPC ........ *A61B 5/02438* (2013.01); *A61B 5/0404* (2013.01); *A61B 5/4836* (2013.01); *A61B 5/681* (2013.01); *A61B 5/6898* (2013.01); *A61N 1/0456* (2013.01); *A61N 1/0484* (2013.01); *A61N 1/36014* (2013.01); *A61N 1/36592* (2013.01)

(58) Field of Classification Search

CPC .... A61B 5/681; A61B 5/6898; A61N 1/0456; A61N 1/0484; A61N 1/36014; A61N 1/3625; A61N 1/36592

See application file for complete search history.

(56) References Cited

U.S. PATENT DOCUMENTS

| | | | |
|---|---|---|---|
| 4,981,146 | A | 1/1991 | Bertolucci |
| 5,226,425 | A | 7/1993 | Righter |
| 5,738,104 | A | 4/1998 | Lo et al. |
| 6,950,695 | B2 | 9/2005 | Chen |
| 2001/0020177 | A1 | 9/2001 | Gruzdowich et al. |
| 2005/0261556 | A1 | 11/2005 | Such et al. |
| 2008/0091256 | A1 | 4/2008 | Libbus et al. |
| 2008/0161883 | A1 | 7/2008 | Conor |
| 2011/0112605 | A1 | 5/2011 | Fahey |
| 2013/0231574 | A1* | 9/2013 | Tran ..................... A61B 5/0022 600/479 |
| 2013/0296723 | A1 | 11/2013 | Cho et al. |
| 2015/0018660 | A1 | 1/2015 | Thomson et al. |
| 2015/0202435 | A1 | 7/2015 | Stuerzinger et al. |
| 2015/0297134 | A1 | 10/2015 | Albert et al. |
| 2015/0306373 | A1 | 10/2015 | Bouton et al. |
| 2015/0309535 | A1 | 10/2015 | Connor |
| 2016/0113578 | A1 | 4/2016 | Eom et al. |
| 2017/0157398 | A1 | 6/2017 | Wong et al. |
| 2018/0028809 | A1 | 2/2018 | Ziv |

FOREIGN PATENT DOCUMENTS

| | | | |
|---|---|---|---|
| WO | 0105464 | A1 | 1/2001 |
| WO | 2017208167 | A1 | 12/2017 |

OTHER PUBLICATIONS

Marek Malik, "Heart rate variability, Standards of Measurement, Physiological Interpretation, and Clinical Use", Circulation, vol. 93, No. 5, 1996, 1043-1065.

Jacqueline M. Dekker et al., "Low Heart Rate Variability in a 2-Minute Rhythm Strip Predicts Risk of Coronary Heart Disease and Mortality From Several Causes", Circulation, 2000; 102: 1239-1244.

Juha Perkiomaki et al., "Heart Rate Variability Findings as a Predictor of Atrial Fibrillation in Middle-Aged Population", Journal of Cardiovascular Electrophysiology, 25(7): 719-24: 2014.

International Search Report PCT/IL2016/051036 Completed Jan. 8, 2017; dated Jan. 9, 2017 3 pages.

Written Opinion PCT/IL2016/051036 Completed Jan. 8, 2017; dated Jan. 9, 2017 5 pages.

Communication about intention to grant dated Jan. 31, 2020, which issued during the prosecution of Applicant's Europe patent application No. 16848262.8.

* cited by examiner

Patient Information

| Date | 2016/7/12 20:02:00 | Gender | Female |
|---|---|---|---|
| ID | 20160713010204 | Age | 46 |
| Name | | | |

Result

| Time Domain Analysis | | Frequency Domain Analysis | | | |
|---|---|---|---|---|---|
| Mean HRT (bpm) | 73 | TP (ms2) | 997.648 | LF Norm (n.u.) | 89.673 |
| SDNN (ms) | 37.692 | VLF (ms2) | 354.348 | HF Norm (n.u.) | 35.254 |
| RMSSD (ms) | 26.465 | LF (ms2) | 576.868 | LF/HF | 2.544 |
| PSI | 88.663 | HF (ms2) | 226.790 | | |

Presure Index — Normal / High

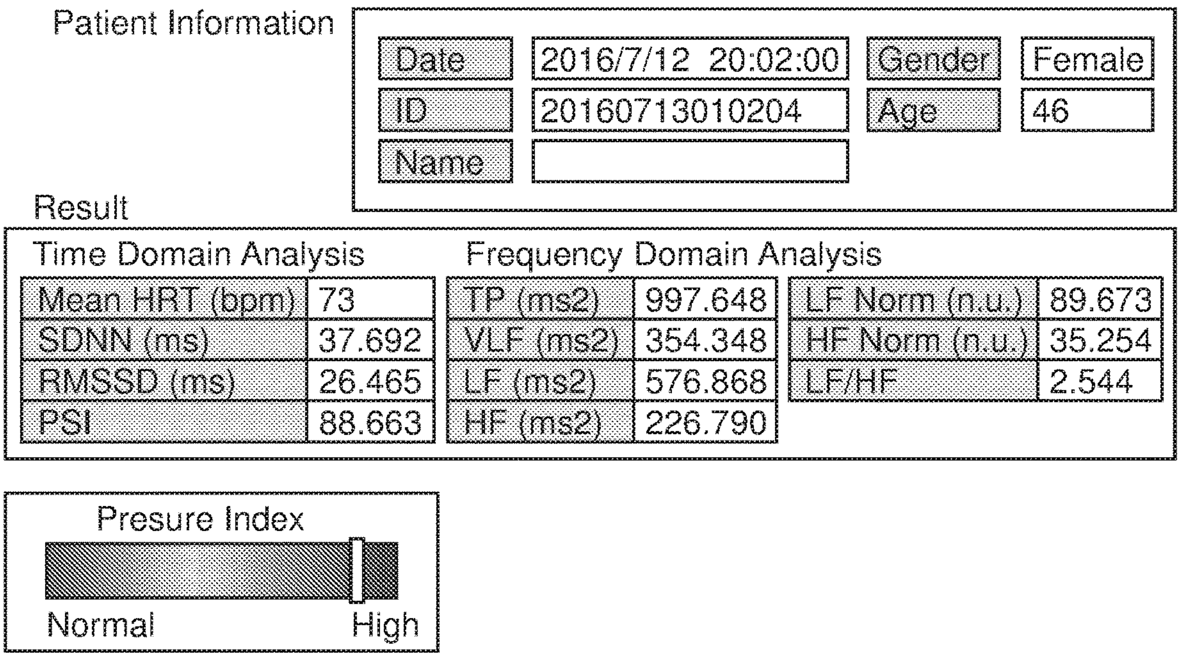

FIG. 5a

Patient Information

| Date | 2016/7/12 20:48:08 | Gender | Female |
|---|---|---|---|
| ID | 20160713014812 | Age | 46 |
| Name | | | |

Result

| Time Domain Analysis | | Frequency Domain Analysis | | | |
|---|---|---|---|---|---|
| Mean HRT (bpm) | 63 | TP (ms2) | 3542.154 | LF Norm (n.u.) | 89.706 |
| SDNN (ms) | 71.558 | VLF (ms2) | 214.820 | HF Norm (n.u.) | 12.124 |
| RMSSD (ms) | 48.935 | LF (ms2) | 2984.830 | LF/HF | 7.399 |
| PSI | 68.453 | HF (ms2) | 403.411 | | |

Presure Index — Normal / High

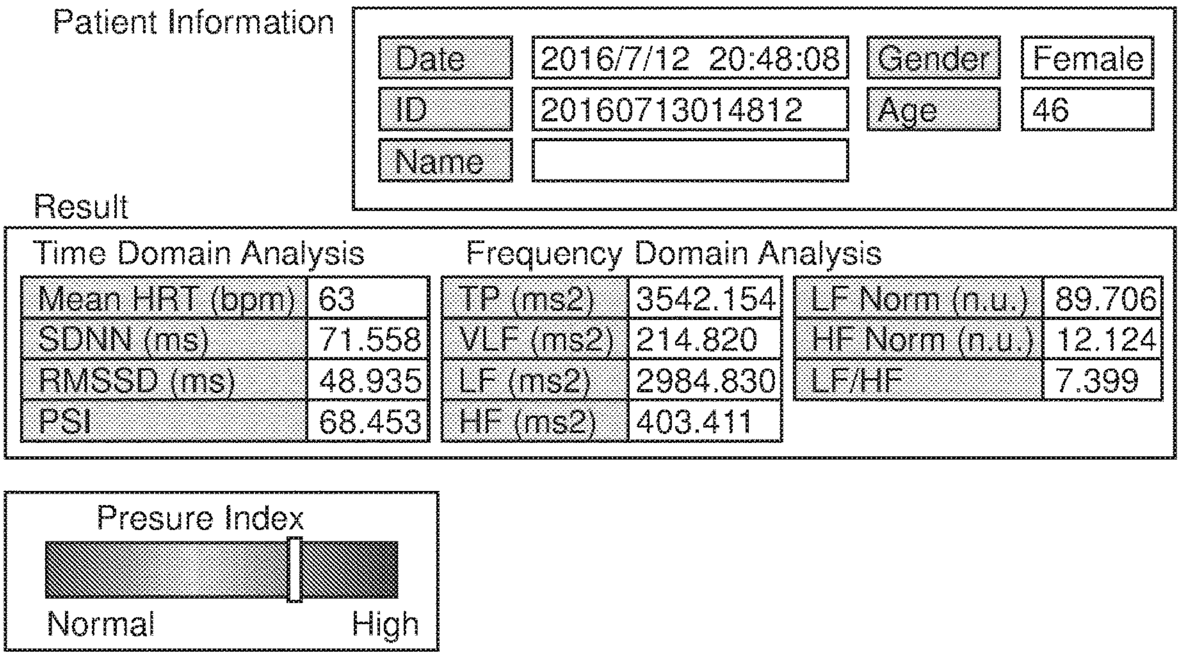

FIG. 5b

MONITORING AND STIMULATION MODULE

RELATED APPLICATIONS

This application is a National Phase of PCT Patent Application No. PCT/IL2016/051036 having International filing date of Sep. 20, 2016, which claims the benefit of priority of U.S. Patent Application No. 62/221,152 filed on Sep. 21, 2015. The contents of the above applications are all incorporated by reference as if fully set forth herein in their entirety.

FIELD OF THE INVENTION

The present disclosure, in some embodiments, relates to the field of devices for monitoring and treating heart parameters, and more particularly, but not exclusively, to wearable devices for monitoring and treating heart parameters.

BACKGROUND OF THE INVENTION

Heart-rate variability (HRV) refers to the phenomenon of variation in the time intervals between normal heart beats (non-arrhythmic heart beats). In a normal healthy state, the time intervals between successive heart beats may vary significantly during rest or in response to a change in activity (e.g. getting up from a sitting position), indicating a healthy and flexible interplay between the autonomic nervous system and the cardiovascular system. Higher values of HRV parameters, such as the standard deviation of the time intervals between successive normal heart beats (the standard deviation of NN intervals or SDNN), and the square root of the mean of the squares of time intervals between successive normal heart beats (the root-mean-square of successive differences or rMSSD), indicate better health and wellbeing. Lower values of HRV parameters may indicate high stress, poor rest or sleep, as well as certain pathological conditions. In sports and fitness, higher HRV before a workout was shown to induce better performance in the workout. In cardiology, patients with lower HRV after a myocardial infarct were shown to have higher incidence of cardiac arrhythmias and increased all-cause mortality rates. The joint taskforce of the European Society of Cardiology and the North American Society of Pacing and Electrophysiology [Eu. Heart Journal. 17, 354-381; 1996 and Circulation Journal 1; 93(5):1043-65] issued a guidelines statement emphasizing the importance of monitoring HRV and outlined the clinical benefits of HRV improvement. Some research reports [Circulation Journal. 102:1239-1244, 2000] showed that HRV measurements from a 2 minute rhythm strip is sufficient for determining increased risk of cardiovascular morbidity and mortality. Others have reported [Journal of Cardiovascular Electrophysiology 25(7):719-24; 2014] the close relations between HRV and cardiac arrhythmias such as atrial fibrillation (AF) and emphasize the importance of monitoring HRV for preventing cardiac arrhythmias.

Neuromodulation, that is to say, nerve stimulation, may be used to treat various conditions, ranging from psychiatric disorders, such as depression, to physiological conditions, such as chronic pain. In particular, neuromodulation of peripheral nerves may be used to modulate the autonomic nervous system. For example, neuromodulation of the median and ulnar nerves in the forearm may be used to enhance parasympathetic activity of the vagus nerve and depress sympathetic activity of the cardiac nerve, and thereby to reduce heart-rate, regulate heart rhythm, and correct and prevent cardiac arrhythmias. Neuromodulation of the median and ulnar nerves may also be used to induce a neurohormonal response: secretion of endorphins, decrease of stress related hormones, and thereby to reduce stress and improve sleep.

Portable devices for monitoring and treating various physiological conditions allow for real-time treatment, whether in response to an acute crisis, or to effect a general state of wellness and improved mood. Recent years have seen a sharp rise in the number of consumer wearable devices designed to monitor physiological conditions, from devices designed to track vital signs, such as heart-rate or blood pressure, to recreational wearable devices, such as wearable fitness trackers. Many of these devices are aimed at monitoring and are not designed to provide treatment. Specifically, many wearable devices on the market, whether medical or recreational, for monitoring heart activity and function (e.g. heart-rate, HRV) do not offer treatment.

SUMMARY OF THE INVENTION

The present disclosure relates to portable devices for monitoring and/or treating physiological functions. More specifically, aspects of the disclosure, in some embodiments thereof, relate to wearable devices for monitoring and/or influencing heart functions, as well as for affecting neurohormonal balance and autonomic nervous system control and thereby affecting heart-rate, heart rhythm, heart-rate variability (HRV), and overall wellness.

As mentioned above, many commercial portable devices for monitoring heart function do not offer treatment. Provision of immediate, on-the-spot treatment in response to a sudden change in a monitored heart activity may prove crucial in case of an acute cardiac crisis, even if the device is only be able to provide an initial treatment, which will have to be followed by comprehensive treatment, e.g. in a hospital. There is therefore a need for wearable medical devices, with home-care capabilities, which provide continuous monitoring and routine prevention treatments, with provides stimulation and monitoring capabilities in a single device, advantageously allowing for a closed-loop operation for obtaining a desired treatment efficacy. Beyond medical uses, a wearable device capable of both monitoring and treating heart function, as well as enhancing nervous-cardiovascular systems interactions, may also have utility (a) as a wellness aid, due to the above-mentioned inter-relation between heart activity and states of wellness, and (b) as a fitness aid, allowing a user to influence his heart activity and HRV before, during, and after a session of physical exercise, such as to improve sports performance and recovery and thus both reduce the chance for injury as well as enhance overall fitness performance and goals. According to some embodiments, the stimulation parameters may be adjusted based on recently acquired measurement data, for providing a fast adjustment loop, and also may be adjusted based on the history of acquired measurement data, for providing a long-term loop.

Thus, aspects of the disclosure, in some embodiments described herein, include a small and portable module for monitoring and treating heart functions. The module may be used to measure heart rate, HRV, and to conduct electrocardiography (ECG) of a user's heart, and accordingly, based on values of the monitored heart parameters, to provide low-level electrical stimulation of the one or more peripheral nerves, e.g. a median nerve, to modulate heart-rate, heart rhythm, and to improve HRV and optimize neuro-cardio balance. In addition, the module may also be used for wellness purposes, for example, to reduce stress and to improve sleep.

Advantageously, the module is integrated in the sense that monitoring and treatment are not implemented by distinct and separate units within the module, but by a single unit. The single unit has joint components, which are used to implement both monitoring and treatment, thereby saving space and reducing the overall size of the module. Specifically, the module includes at least one dual-function electrode which is used both for monitoring heart parameters and for electrical neuro-stimulation.

In some embodiments, the module may be stand-alone, for example, in the form of wearable element, such as a band designed to be worn on the wrist, arm, forearm, neck, leg, and/or the thigh. In some embodiments, the module may be designed to be attachable to (and detachable from) a smartwear device, such as a smartwatch or a smart-band, or may be designed as an integral part of a smartwear device. The latter two embodiments may facilitate a design wherein the module employs components integral to smartwear devices, such a user interface, a display, a wireless communication unit, batteries, and even computational elements (e.g. processors), thereby further reducing the size of the module.

The module may also be used in conjunction with an external device, such as a user's smartphone, the module being configured to transmit/receive information from the external device. An exemplary neuro-stimulation session, according to the teachings herein, may involve the following steps (performed using the module): (a) measuring electrical signals indicative of heart function/activity such as HRV, (b) transmitting the measurement data to the user's smartphone, wherein the measurement data are processed to obtain electrical stimulation parameters for an ensuing treatment, (c) receiving the electrical stimulation parameters (sent from the smartphone), and (d) applying neuro-stimulation, according to the obtained electrical stimulation parameters.

Thus, according to an aspect of some embodiments, there is provided a portable module for non-invasive electrical neuro-stimulation of one or more peripheral nerves and monitoring of one or more heart parameters of a subject. The portable modules include:

- a monitoring electrode, mounted in/on a top surface of the portable module;
- a stimulation electrode and a dual-function electrode, mounted in/on a bottom surface of the portable module;
- a monitoring unit for monitoring electrical activity;
- a stimulation unit for inducing electrical signals; and
- a control unit
- a non-transitory memory, having stored therein a computer readable code configured to be operated by the control unit Each of the electrodes is at least partly exposed. The control unit is configured to enable controllably switching between at least two modes of operation of the portable module:

- a first mode, wherein the monitoring unit is functionally associated with the monitoring and dual-function electrodes; and
- a second mode, wherein the stimulation unit is functionally associated with the stimulation and dual-function electrodes.

The module is configured to facilitate simultaneously establishing dermal contact between a target body part of the subject and the dual-function electrode, and between an opposing body part (to the target body part) and the monitoring electrode, thereby allowing, in the first mode, to obtain heart parameters of the subject by monitoring electrical activity at the dual-function and monitoring electrodes.

The module is further configured to facilitate establishing dermal contact between the target body part and both of the dual-function electrode and the stimulation electrode, thereby allowing, in the second mode, to electrically neuro-stimulate at least one peripheral nerve in the target body part, by inducing an electrical signal between the dual-function and stimulation electrodes.

In some embodiments, the one or more heart parameters include heart-rate and/or heart-rate variability (HRV).

In some embodiments, the monitoring unit is configured to perform an electrocardiography (ECG) of the subject.

In some embodiments, the module is configured to be independently held against the target body part.

In some embodiments, the target body part is an inner part of a wrist, arm, neck, leg, and/or forearm.

In some embodiments, the at least one peripheral nerve is a median nerve in the wrist.

In some embodiments, the stimulation electrode is a first stimulation electrode and the stimulation signal is a first stimulation signal, and the module further includes a second stimulation electrode mounted in/on the bottom surface, such as to be at least partly exposed and such that the dual-function electrode is positioned between the first stimulation electrode and the second stimulation electrode.

The module is further configured to facilitate establishing dermal contact between the target body part and the second stimulation electrode, thereby allowing, in the second mode, to induce a second stimulation signal, between the dual-function electrode and the second stimulation electrode, optionally simultaneously with, or alternately with, the first stimulation signal, thereby electrically neuro-stimulating the at least one peripheral nerve in the target body part.

In some embodiments, the stimulation electrode is a first stimulation electrode and the stimulation signal is a first stimulation signal, and the module further includes a second stimulation electrode and a third stimulation electrode mounted in/on the bottom surface, such as to be at least partly exposed, and wherein the first stimulation electrode, the dual-function electrode, the third stimulation electrode, and the second stimulation electrode are substantially respectively linearly ordered.

The module is further configured to facilitate establishing dermal contact between the target body part and the second and third stimulation electrodes, thereby allowing, in the second mode, to induce a second stimulation signal, between the third stimulation electrode and the second stimulation electrode, optionally simultaneously with, or alternately with, the first stimulation signal, thereby electrically neuro-stimulating a second peripheral nerve in the target body part.

In some embodiments, wherein the target body part is an inner part of a wrist and the at least one peripheral nerve is a median nerve in the wrist, the second peripheral nerve is an ulnar nerve in the wrist.

In some embodiments, the stimulation signals are characterized by stimulation parameters determined based on the heart parameters obtained in the first mode.

In some embodiments, the stimulation parameters are selected from the group consisting of: frequency, intensity, amplitude, duration, waveform, intermittency, and polarity, of a voltage signal and/or a current signal. In some embodiments, the module is modular, such as to allow removable attachment to a wearable device. In some embodiments, the wearable device is a smart-band, or a smartwatch, including a processing circuitry, and the module and the wearable device are functionally associated. In some embodiments, the module is further configured to be controllable via a user interface of the wearable device. In some embodiments, the monitoring electrode is at least partly exposed on an outer surface of the wearable element, and wherein the dual-function and stimulation electrodes are at least partly exposed on an inner surface of the wearable element.

According to an aspect of some embodiments, there is provided a wearable device including the module, as described above, and a band, configured to be worn around a limb of the subject. The band has an inner surface and an outer surface. The monitoring electrode, is at least partly exposed on the outer surface and the dual-function and stimulation electrodes are at least partly exposed on the inner surface. The target body part is located within the limb.

In some embodiments, the band further includes a user interface, configured to facilitate control over the operation of the module. In some embodiments, the user interface includes a display, configured to provide graphical indications related to the operation of the module. In some embodiments, the graphical indications include the heart parameters obtained in the first mode and/or the stimulation parameters obtained in the second mode. In some embodiments, the user interface is configured to display during the second mode an ECG/HR/HRV reading of the subject. In some embodiments, the wearable device further includes a battery for providing electric power to sustain the operation thereof. In some embodiments, the band further includes a communication unit, configured to facilitate data and/or control communication with an external module or compute element, such as a smart-phone, a computer, a cloud server or the like.

According to an aspect of some embodiments, there is provided a method for operating the wearable device as previously disclosed, including the steps of:

- fastening the wearable element around a wrist of a subject, such that the stimulation electrode and the dual-function electrode are in dermal contact with an inner part of the wrist, with the dual-function electrode being located proximately to a median and/or an ulnar nerve in the wrist;
- selecting a first mode of operation and bringing an opposing body part into contact with the monitoring electrode;
- measuring heart-related activity of the subject by monitoring electrical activity between the monitoring electrode and the dual-function electrode
- Analyzing the monitored data by a processing unit and determining heart parameters therefrom;
- determining stimulation parameters based on the heart parameters;
- selecting a second mode of operation, and applying electrical stimulation at the inner part of the wrist by generating a stimulation signal between the stimulation electrode and the dual-function electrode.

In some embodiments, the method further includes, subsequently to said step of selecting the second mode of operation, reapplying said steps of selecting the first mode of operation, measuring the heart-related activity, and determining the stimulation parameters, thereby obtaining updated heart parameters, and accordingly adjusting the stimulation parameters.

Certain embodiments of the present invention may include some, all, or none of the above advantages. Further advantages may be readily apparent to those skilled in the art from the figures, descriptions, and claims included herein.

Aspects and embodiments of the invention are further described in the specification hereinbelow and in the appended claims.

Embodiments of methods and/or devices herein may involve performing or completing selected tasks manually, automatically, or a combination thereof. Some embodiments are implemented with the use of components that comprise hardware, software, firmware or combinations thereof. In some embodiments, some components are general-purpose components such as general purpose computers or processors. In some embodiments, some components are dedicated or custom components such as circuits, integrated circuits or software.

For example, in some embodiments, some of an embodiment may be implemented as a plurality of software instructions executed by a data processor, for example, which is part of a general-purpose or custom computer. In some embodiments, the data processor or computer may comprise volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results).

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIGS. 5*a*-5*b* depict results of monitoring heart parameters before and after treatment using a second-generation model of the wearable element of FIG. 4*a* on a single subject;

DETAILED DESCRIPTION OF SOME EMBODIMENTS

Figure 1A:
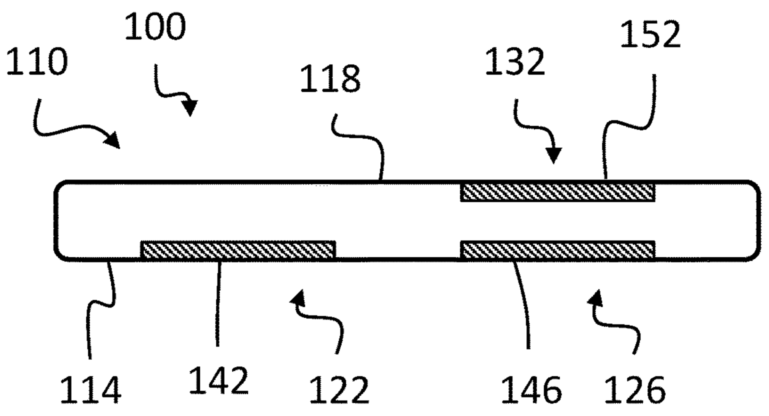
FIG. 1*a* schematically depicts a side-view of a module embodiment of the disclosure, according to some embodiments.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The principles, uses and implementations of the teachings herein may be better understood with reference to the accompanying description and figures. Upon perusal of the description and figures present herein, one skilled in the art is able to implement the teachings herein without undue effort or experimentation. In the figures, like reference numerals may refer to like parts throughout.

As used herein, "treatment" may refer to an altering, a modification, an effecting, a modulating, and/or a handling action for one or more physiological conditions, states, properties, characters, functions, and/or activities. "Heart function" and "heart activity" are used interchangeably. "Heart function parameters/heart activity parameters/heart parameters" may refer to parameters used to evaluate/estimate/quantify heart-rate and heart-rate variability, and/or obtain/measure ECG, as elaborated on hereinbelow.

As used herein, "electrical neuromodulation" may be interchangeable with the terms "neuromodulation" and "neuro-stimulation" and may refer to electrically/electromagnetically/electromechanically, noninvasively/nonintruisively, neuro-modulating neural structures or nerves, that is to say, low-level electrical nerve stimulation.

As used herein, the term "association" between two or more elements (e.g. two electrodes, an electrode and a processing circuitry, a measuring device and a processor and the like) may refer to a physical connection, a functional association, an electrical association, a mechanical association, and/or an electromechanical association between the elements, and the like, and/or any combination thereof.

As used herein, the terms "wearable element" and "wearable device" may be used interchangeably.

As used here, the terms "user", "subject", and "patient" may be used interchangeably.

Figure 1B:
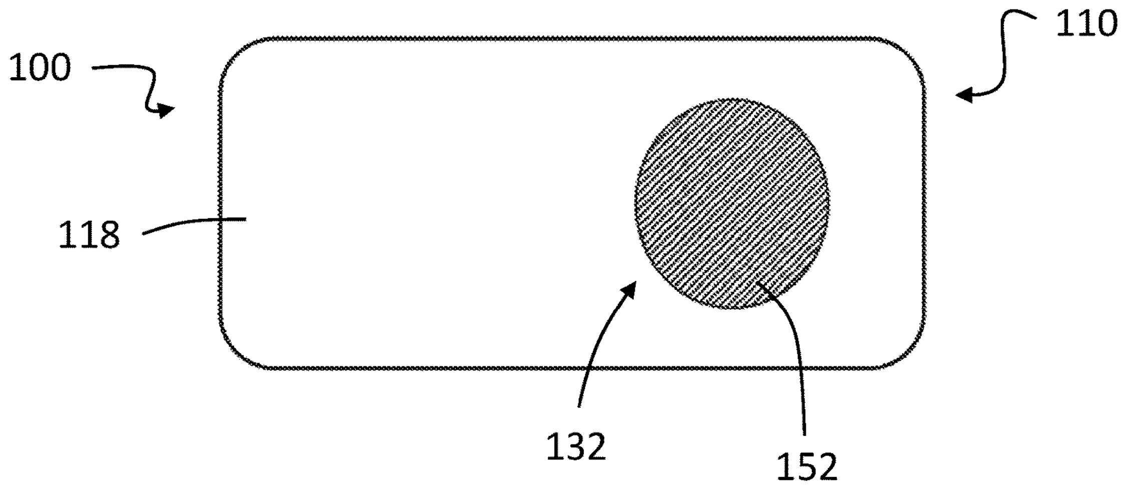
FIG. 1*b* schematically depicts a top-view of the module of FIG. 1*a*, according to some embodiments.
Figure 1C:
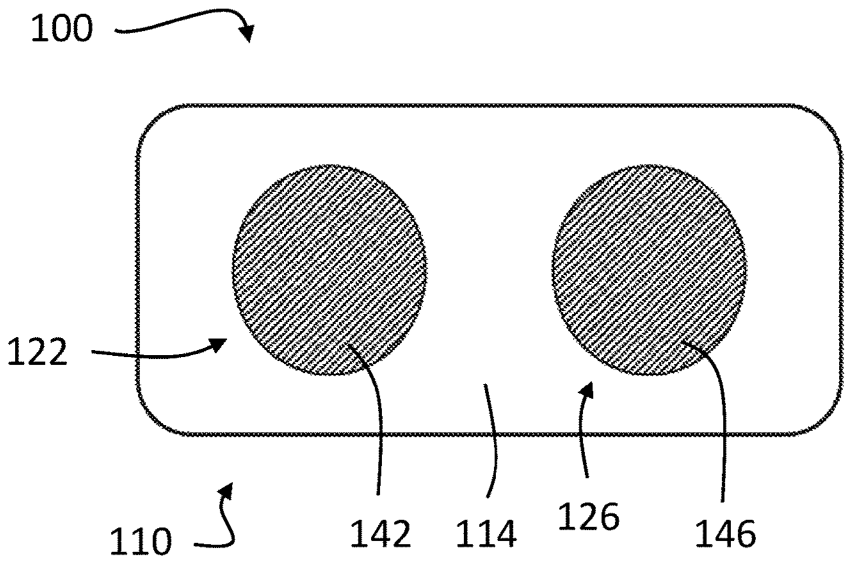
FIG. 1*c* schematically depicts a bottom-view of the module of FIG. 1*a*, according to some embodiments.

A first embodiment of the disclosure, as described herein, is schematically depicted in FIGS. 1*a*-1*c*. FIG. 1*a* schematically depicts a side-view of a module 100, according to some embodiments. Module 100 includes a module body 110. Module body 110 includes two opposite surfaces: an inner surface 114 (a bottom surface), and an outer surface 118 (a top surface). A stimulation electrode 122 and a dual-function electrode 126 are mounted in/on module body 110 on inner surface 114, such that an external surface 142 of stimulation electrode 122 and an external surface 146 of dual-function electrode 126 are both exposed. A monitoring electrode 132 is mounted in/on module body 110 on outer surface 118, such that an external surface 152 of monitoring electrode 132 is exposed. In some embodiments, stimulation electrode 122 and dual-function electrode 126 protrude from inner surface 114, and/or monitoring electrode 132 protrudes from outer surface 118.

FIG. 1*b* and FIG. 1*c* schematically depict a top-view and a bottom-view of module 100, showing outer surface 118 and inner surface 114, respectively, according to some embodiments.

Module 100 is configured to allow switching between two modes of operation. In a first mode of operation (a "monitoring mode"), monitoring electrode 132 and dual-function electrode 126 are electrically associated. In a second mode of operation (a "stimulation mode"), stimulation electrode 122 and dual-function electrode 126 are electrically associated and may have opposite polarities, respectively.

In some embodiments, module 100 is configured to be held against or placed on a target body part of a user such that stimulation electrode 122 and dual-function electrode 126 are both in dermal contact with the target body part, and such that the user may simultaneously make dermal contact with monitoring electrode 132 by touching it with an opposing body part.

As used herein, "dermal contact" between a conducting object and a body part may refer to direct contact between skin on the body part and the conducting object, as well as to indirect contact between the skin on the body part and the conducting object (for example, via a gel layer, saline solution, or the like, in between the object and the body part, or a medium carrying or soaked with such liquids), which allows for electrically associating the conducting object with the body part.

Two body parts (such as a right arm and a left leg, a pair of forearms, a right finger and a left finger, or a right finger and left forearm, and so on), or a "first body part" and a "second body part", may be said to be "opposing" when located to the left of the heart and to the right of the heart of a user, respectively, such as to allow performing an ECG on the user by obtaining electric signals from the first body part and the second body part, respectively (for example, by monitoring the potential difference between the left wrist (the first body part) and the right index finger (the second body part)). "Two distinct body parts" may refer to a "target body part" (which may be used interchangeably with "first body part") and an "opposing body part" (which may be used interchangeably with "second body part").

In the first mode of operation, an ECG on the user may be performed by bringing dual-function electrode 126 and monitoring electrode 132 into dermal contact with a first body part and a second body part, respectively, and for example, monitoring temporal variations, in the potential difference between dual-function electrode 126 and monitoring electrode 132, using, for example, a voltmeter/potentiometer associated therewith, as elaborated on below.

In the second mode of operation, stimulation electrode 122 and dual-function electrode 126 are connected to two opposite (polarity) terminals, respectively, of an electric power source. An electric current may be induced through the target body part, particularly, through or near a target nerve, by establishing a potential difference between stimulation electrode 122 and dual-function electrode 126, as elaborated on below.

In some embodiments, module body 110 is flexible. In some embodiments, outer surface 118 is parallel to inner surface 114. In some embodiments, module body 110 is bent or concave. In some embodiments, monitoring electrode 132 is located opposite to dual-function electrode 126. In some embodiments, each of the electrodes has a different diameter. In some embodiments, module body 110 is made of plastic or other polymer-based material. In some embodiments, the electrodes are made of a non-corrosive metal, such as a stainless-steel alloy. In some embodiments, the electrodes may be coated with a non-stick and conductive coating material.

In some embodiments, module 100 is wearable, or configured to be mechanically associated with/installed in a wearable device/element. The module (in embodiments wherein the module is wearable) or the wearable device may be shaped, for example, as a bracelet, a band, a cuff, a ring, a belt, a collar, or a chain. In some embodiments, the module may be embedded within a shirt and/or pants (for example, in a sleeve of the shirt), or within a glove or a sock. In some embodiments, the module may be independently held using a removable patch, sticker, or adhesive bandage, fitted such that stimulation electrode 122 and dual-function electrode 126 are in dermal contact with the first body part and external surface 152 remains exposed and reachable by the second body part.

As used herein, an object may be referred to as being "independently held" against a body part when—following the placing thereof against, or the attaching thereof to, the body part—the object is kept in place without any action on the part of the user. Accordingly, for example, a watch may be said to be independently held about a wrist when prevented of slipping off the wrist due to being fastened thereabout. In contrast, a watch held in hand (and not fastened about the wrist) is not independently held. As used herein, the terms "held" and "independently held" may be interchangeable according to context.

In some embodiments, module 100 is configured to facilitate administering treatment to (and to be independently held against) different body parts (as well as performing monitoring thereon), in particular, differently shaped body parts. In some such embodiments, module 100 is flexible, the flexibility thereof allowing to establish dermal contact between electrodes 122 and 126 and differently shaped body parts (such as an arm and the back).

Figure 2:
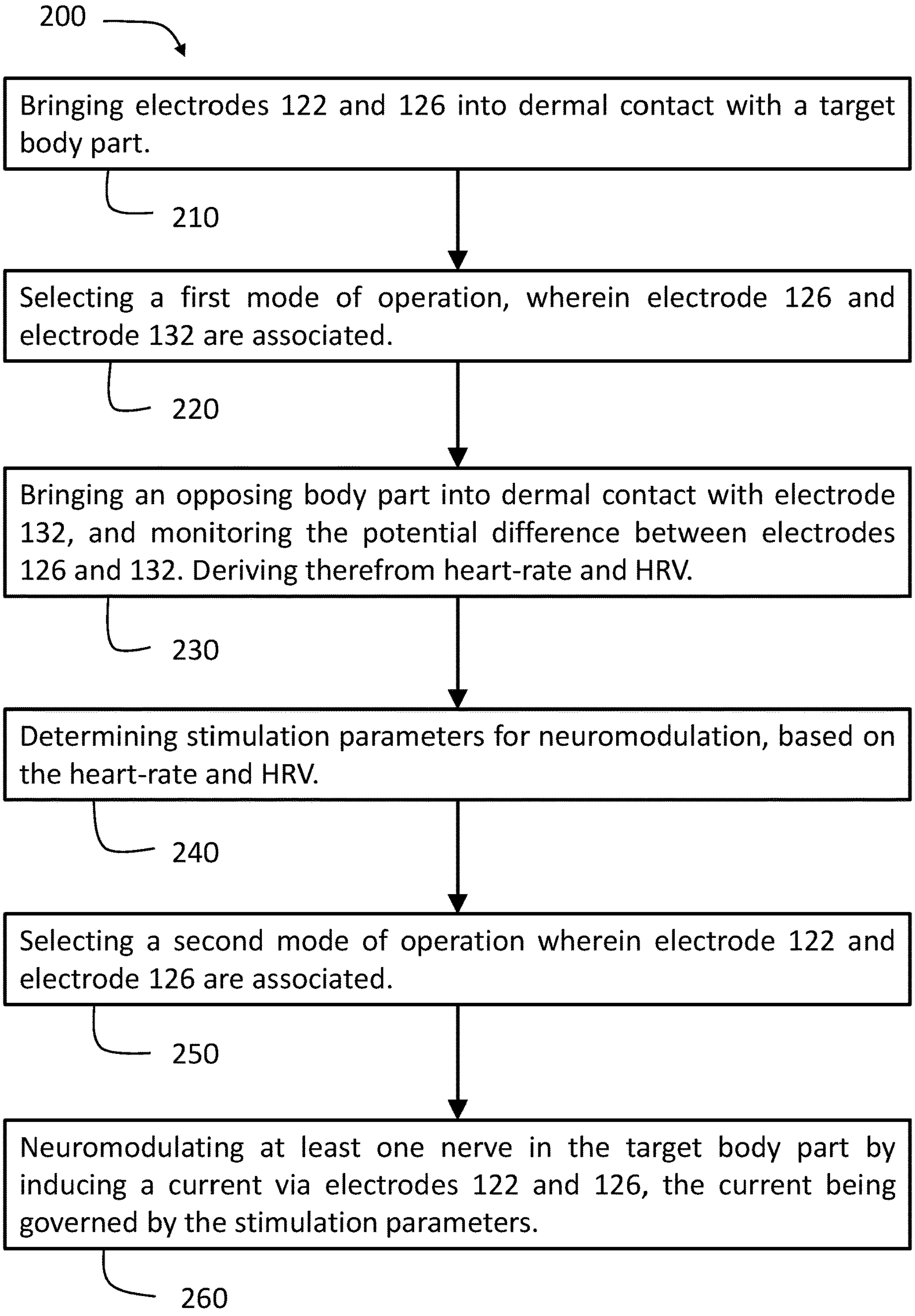
FIG. 2 schematically depicts a method of operating the module of FIGS. 1*a*-1*c*, according to some embodiments.

FIG. 2 presents a method 200 of operating module 100, according to some embodiments. In a step 210, stimulation electrode 122 and dual-function electrode 126 are brought into dermal contact with the target body part (the first body part) by bringing inner surface 114 against the target body part.

In a step 220, the first mode of operation is selected.

In a step 230, the user places an opposing body part (a second body part), such as a finger or an inner part of a forearm (opposing the target body part), on monitoring electrode 132. A potential difference between monitoring electrode 132 and dual-function electrode 126 is measured, thereby performing an ECG on the user. When the ECG is completed (which, in some embodiments, may be graphically and/or audibly indicated by a user-interface included in module 100 or a user-interface on an external agent, external device, associated therewith), the user removes the opposing body part from monitoring electrode 132. Values for monitored heart function parameters ("heart parameters" for short) such as the heart-rate and the HRV, are obtained from the measured temporal variations in the potential difference, as elaborated on below.

In a step 240, electrical stimulation parameters ("stimulation parameters" for short) for a follow-up neuromodulation applied at the target body part, such as a current intensity, duration and/or a frequency of an alternating current, are determined based on the obtained values of the monitored heart parameters, as elaborated on below.

In a step 250, the second mode of operation is selected.

In a step 260, neuromodulation of at least one nerve in the target body part (e.g. the median nerve in the left wrist) is effected by applying an electric stimulation signal ("stimulation signal" for short) between stimulation electrode 122 and dual-function electrode 126 (which have opposite polarities, respectively). More specifically, an electric current is conducted via a conduction pathway, including stimulation electrode 122, dual-function electrode 126, and a region near, or including (possibly partially), a segment of the at least one nerve. By default, the stimulation signal is characterized by the stimulation parameters determined in step 240, but the user may decide to manually modify the stimulation parameters or to select different stimulation parameters.

The term "stimulation signal", with reference to electrical neuro-stimulation, refers to a voltage/current signal applied between a pair of electrodes (attached to a target body part, such as to electrically neuro-stimulate at least one nerve therein the target body part). The term "stimulation parameters", with reference to a stimulation signal, refers to parameters characterizing the stimulation signal, including duration, amplitude, maximum intensity, frequency, and waveform of the stimulation signal, as well as waveforms and inter-pulse time intervals when the stimulation signal comprises a series of pulses. It is noted that the term "stimulation parameters" is used in a broad sense to encompass also one or more time-dependent functions. For example, a sine wave function may be characterized by the amplitude, frequency, and phase thereof, but the term "stimulation parameters" will also be used to cover functions having a more complex waveform, as well as discrete functions.

In some embodiments, step 260 may involve application of an intermittent stimulation signal (i.e. a voltage/current signal), that is to say, a series of electric pulses (each electric pulse essentially being a brief duration stimulation signal). In some embodiments, the time intervals between successive electric pulses ("stimulation pulses") and the shape (i.e. the modulation, the waveform) of each pulse may be controllably varied either automatically, or manually. In some embodiments, the stimulation pulses may be biphasic, that is to say, that a positive voltage portion of a pulse is followed, substantially immediately, by a negative voltage portion of the pulse. In some embodiments, the area covered by the positive voltage (indicative of conducted charge) portion is substantially equal to the area covered by the negative portion, thereby preventing/minimizing occurrence of electrolysis (which may result from the flow of electric currents through bodily tissue (in the target body part) containing fluids) when the pulse width is sufficiently narrow (e.g. smaller than 1 msec).

In some embodiments, step 260 additionally or alternatively involves application of a continuous stimulation signal.

In some embodiments, as little as 15 seconds are required to measure the heart-rate, as little as 30 seconds are required to obtain an ECG reading, and as little as 60 seconds are required to measure the HRV. In some embodiments, as little as 1 minute of neuromodulation may be sufficient affect heart function or to effect a state of wellness. A stimulation session (that is to say, an application of a method, such as method 200, using a module, such as module 100), including both monitoring and neuromodulation, may take about 6-7 minutes. Longer or shorter durations of monitoring and treatment may also be applied (for example, periods may be in seconds, minutes, days, weeks, months, or years for continuous monitoring and treatment).

As used herein, "heart-rate" is defined as a number of heart beats per unit time as measured by the number of RR peaks in an ECG strip or a pulse reading. "RR interval" (RR) is the interval between successive peaks of an ECG signal. "Heart rate variability" (HRV) refers to the phenomenon of variation in the time intervals between successive normal heart beats (non-arrhythmic heart beats), and may be quantified by the SDNN, rMSSD, or pNN50, which are defined below.

In some embodiments, the following set of data may be obtained from the ECG or heart-rate measurement in step 230: HRV, RR, AVNN, SDNN, rMSSD, pNN50, LF, and HF. Time domain HRV analysis parameters include: "NN interval" ("normal to normal interval") is defined as the time interval between successive normal beats (in msec). "Average NN" (AVNN) is defined as the mean of a set of NN intervals. "Standard deviation of NN" (SDNN ms) is defined as the standard deviation of a set of NN intervals and represents parasympathetic (calming down) activity of the autonomic nervous system. "Root mean square of successive differences" (rMSSD msec) is defined as the square root of the mean of squares of differences between adjacent (successive) NN intervals in a set of NN intervals and also represents parasympathetic (calming down) activity of the autonomic nervous system. "NN50" is defined as the number of pairs of successive NN intervals, which differ by more than 50 msec, in a set of NN intervals. "Percentage and/or proportion of NN50" (pNN50) is defined as NN50 divided by a total number successive of NN intervals in the set. Frequency domain HRV parameters include: "Low-frequency activity" (LF $ms^2$) is defined as the total power of the low-frequency Fourier coefficients, i.e. 0.04-0.15 Hz in an ECG reading and represents parasympathetic activity of the autonomic nervous system or in the reading of any other heart-rate monitoring system, such as a heart-rate tracker or the like, including monitoring systems based on electrical measurements, optical measurements, pressure measurements, or any other type of measurements and methods, wherein the total power is defined as a sum of the absolute value squared of all the Fourier coefficients in the range. "High-frequency activity" (HF $ms^2$) is defined as the total power of the high-frequency Fourier coefficients, i.e. 0.15-0.4 Hz, of the reading of a heart-rate monitoring system and represents sympathetic (speeding up) activity of the autonomic nervous system. LF and HF may also be calculated and presented in n.u., The ratio of LF to HF (LF/HF ratio) is an important measurement calculated by the system as it conveys the balance between the sympathetic and parasympathetic systems and their direct effect on heart rate and rhythm. Other frequency domain parameters such as TP ($ms^2$) and VLF ($ms^2$) may also be calculated.

In some embodiments, module 100 may be used for implementing monitoring without implementing neuromodulation and vice-versa. For example, based on the values of the monitored heart parameters (obtained in step 230), the user may decide to skip neuromodulation, or, based on the values of the monitored heart parameters, it may be determined in step 240 that no neuromodulation is required.

In some embodiments, the user may manually select the stimulation parameters, skipping steps 210 to 240. For example, the user may select saved stimulation parameters of a previous session. In some embodiments, the user may select a stimulation setting from a number of default stimulation settings, skipping steps 210 to 240. Each of the default stimulation settings may be based on a different set of stimulation parameters.

In some embodiments, module 100 is configured to send information to, and to receive information from, an external agent (an external device), such as a user's smartphone, smartwatch, home hub, by wireless communication or by wired communication (e.g. by a USB cable). Measurement data, e.g. measured variations in the potential difference between dual-function electrode 126 and monitoring electrode 132, are sent to the external agent, suc as a smartphone, a computer, a cloud server or the like, wherein the measurement data is processed to obtain the values of the monitored heart parameters in step 230. The determination of stimulation parameters in step 240, is also performed by the external agent using the obtained values of the monitored heart parameters. The obtained values of the monitored heart parameters ("acquired data" for short) and the stimulation parameters may be stored in a memory on the external agent for future reference, as described hereinbelow. Stimulation parameters may also be transmitted from the external agent directly to module 100 independently of the acquired data, e.g. preset parameters of a certain stimulation regiment/protocol to achieve a desired physiological effect.

In some embodiments, method 200 may involve switching/alternating between the stimulation mode and the monitoring mode. Following a (preset) period of stimulation, the module may automatically switch back to the monitoring mode to obtain updated values of the monitored heart parameters. The stimulation parameters are accordingly adjusted (i.e. taking into account the updated values). The module may then switch back to the stimulation mode and resume applying stimulation, and so on.

In some embodiments, the stimulation parameters may be adjusted according to data acquired by an external monitoring device in response to a specific physiological state. The module may provide an automatic stimulation feedback response according to acquired information from the module during the monitoring mode, or additionally/alternatively from an external monitoring apparatus. For example, the module may be programmed to administer an electrical current signal having a low frequency, i.e. 0.1-5.0 Hz, when the obtained HRV reading is low (i.e. lower than normal values as indicated by cardiology guidelines mentioned above), and to administer an electrical stimulation current having a high frequency, for example 5-200 Hz, when the HRV reading is high, or vice-versa, thereby respectively increasing and decreasing HRV, and thus providing an automatic feedback response method for optimizing stimulation parameters based on updated values of monitored heart function parameters. Other stimulation parameters and monitored heart parameters may also be used.

In some such embodiments, method 200 includes round-the-clock monitoring and treatment, and module 100 is configured to allow for such a mode of operation. The monitoring may be continuous or scheduled, for example, every predetermined number of minutes or hours, as advised by a health care provider. In some embodiments, the acquired data from the monitoring mode and the values of the electrical stimulation parameters, used in each stimulation session, may be recorded and patterns and sequences of successful individual electrical stimulation parameters may be stored, e.g. in the external device's memory, for future treatments, such an external device may be a smartphone, a smartwatch, a computer, a cloud server or the like. In some embodiments, the external device includes artificial learning capabilities that allows a module, such as module 100, to identify successful stimulation sessions thus customizing and optimizing the treatment to personal, individual needs, in some embodiments, the artificial learning capabilities are based on data stored and analyzed on the cloud server.

In some embodiments, module 100 is configured to measure additional quantities beyond the potential difference between the electrodes, such as current passing between the electrodes, magnetism, impedance changes, and the like. In some embodiments, in step 230, additional quantities beyond the potential difference between the electrodes may be measured and the stimulation parameters, determined in step 240, are determined taking into account also the measurement data of the additional quantities. Alternatively to ECG, module 100 may facilitate obtaining the heart-rate by measuring variations in impedance incurred by the pulse wave of blood flow in an artery.

In some embodiments, module 100 further includes one or more additional heart function monitoring components, configured to monitor heart function by implementing, for example, optical measurements or blood pressure measurements. The values of at least one of the heart functions, monitored using dual-function electrode 126 and monitoring electrode 132, may be obtained by taking into account also measurement data of the one or more additional heart function monitoring components, thereby possibly allowing for improved heart parameters determination/estimation.

Advantageously, the module, or device may be capable both monitoring and treating heart function, as well as enhancing nervous-cardiovascular systems interactions, and may also have utility (a) as a wellness aid, due to the above-mentioned inter-relation between heart activity and states of wellness, and (b) as a fitness aid, allowing a user to influence his heart activity and HRV before, during, and after a session of physical exercise, such as to improve sports performance and recovery and thus both reduce the chance for injury as well as enhance overall fitness performance and goals. According to some embodiments, the stimulation parameters may be adjusted based on recently acquired measurement data, for providing a fast adjustment loop, and also may be adjusted based on the history of acquired measurement data, for providing a long-term loop.

Figure 3:
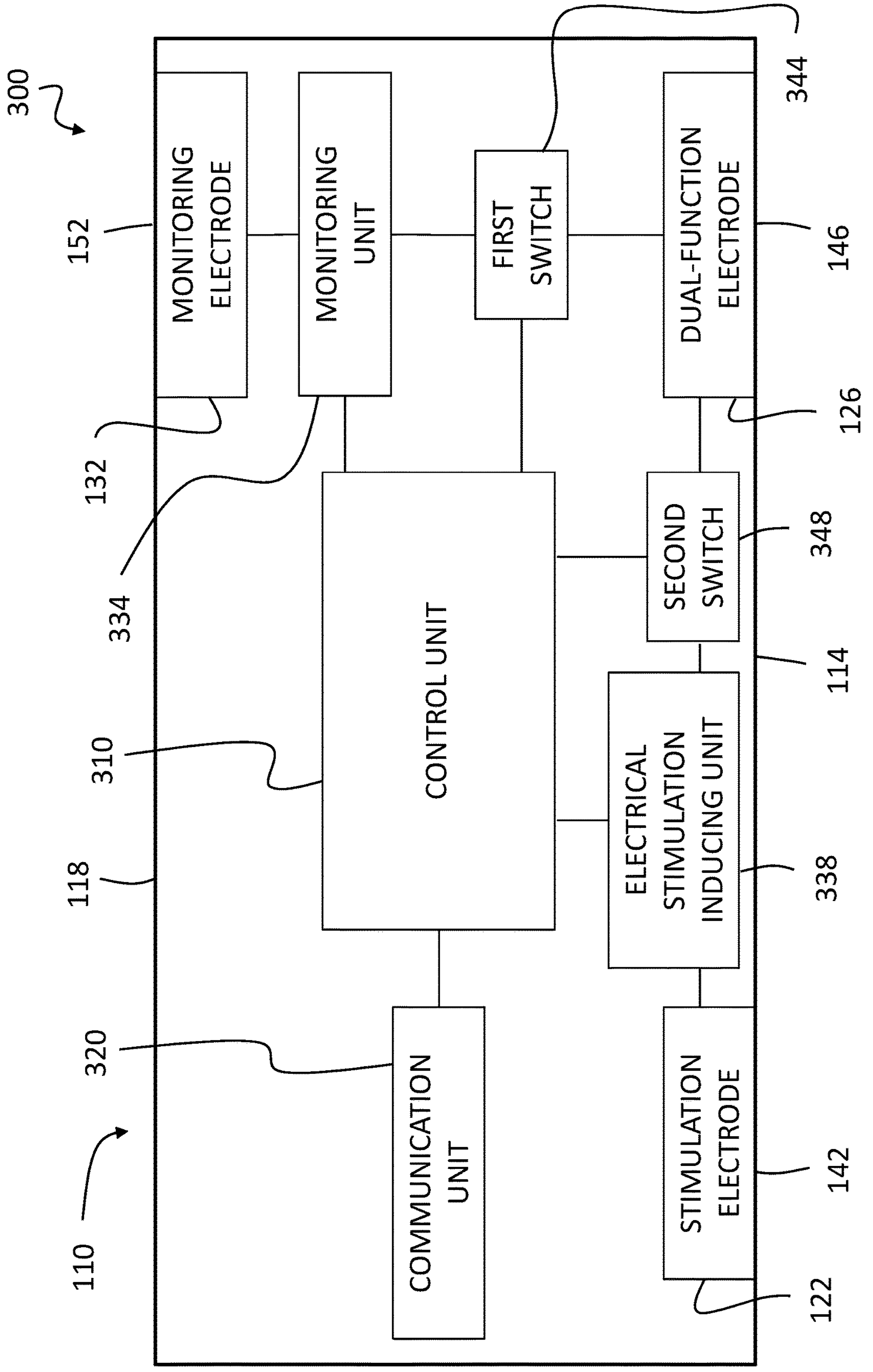
FIG. 3 schematically depicts internal circuitry of a module embodiment of the disclosure, according to some embodiments.

Reference is now made to FIG. 3, which schematically depicts internal circuitry of a module 300, according to some embodiments. Module 300 provides an example embodiment of module 100 (and includes all numbered components thereof (shown in FIGS. 1*a*-1*c*)). Module 300 further includes a control unit 310, a communication unit 320, a heart function monitoring unit 334 ("monitoring unit 334" for short) including a voltmeter/potentiometer (not shown), an electrical stimulation inducing unit 338 ("stimulation unit 338" for short) including an electric power source (not shown), a first switch 344, and a second switch 348.

As used herein, "voltmeter" or "potentiometer" may refer to a device for measuring an electrical potential difference between at least two locations, including analog voltmeters such as a galvanometer, digital voltmeters, field-effect transistors voltmeters (FET-VM), oscilloscopes, and the like. In some embodiments, the measurement may be continuous and/or intermittent. In some embodiments, the potential difference may be discretely sampled. As used herein, "electric power source" may refer to a device capable of inducing a current and/or a potential difference between two locations, including batteries, EMF sources, direct current (DC) sources, alternating current (AC) sources, devices generating currents via electromagnetic induction, and the like. As used herein, the term "switch" may refer to an element for facilitating control and/or signaling for the purpose of control of one of more functions and/or parameters of the module or parts thereof. In some embodiments, a switch may facilitate controllable electrical association between at least two parts of the module.

Communication unit 320, monitoring unit 334, stimulation unit 338, first switch 344, and second switch 348, are associated with control unit 310. Stimulation unit 338 is further associated with stimulation electrode 122 and with second switch 348. Dual-function electrode 126 is further associated with first switch 344 and with second switch 348. Monitoring unit 334 is further associated with first switch 344 and with monitoring electrode 132. Associated elements are shown connected by straight solid lines (not numbered). The architecture of the association described herein is exemplary, and other association architectures may apply.

In some embodiments, a control unit, such as control unit 310, includes processing circuitry and a memory (both not shown). The processing circuitry may be an application specific integrated circuitry (ASIC), a programmable processing circuitry such as an FPGA, firmware, and/or the like. In some embodiments, the memory is a non-transitory memory. The memory may include a solid-state memory, a magnetic memory, a photonic memory, and/or the like. In some embodiments, the memory is a transitory memory. The control unit may further include at least one filter configured to filter electric signals, at least one voltage and/or current amplifier, at least one analog to digital electrical signal convertor, and/or at least one digital to analog electrical signal convertor (not shown).

First switch 344 is configured to controllably electrically associate and dissociate monitoring unit 334 and dual-function electrode 126, and thereby to controllably associate and dissociate monitoring electrode 132 and dual-function electrode 126. Second switch 348 is configured to controllably electrically associate and dissociate stimulation unit 338 and dual-function electrode 126, and thereby to controllably associate and dissociate stimulation electrode 122 and dual-function electrode 126. First switch 344 and second switch 348 are controlled by control unit 310.

In the first mode of operation, dual-function electrode 126 is electrically dissociated from stimulation unit 338 and is electrically associated with monitoring unit 334, thereby facilitating measurement of a potential difference between monitoring electrode 132 and dual-function electrode 126. In the second mode of operation, dual-function electrode 126 is electrically dissociated from monitoring unit 334 and is electrically associated with stimulation unit 338, thereby facilitating electrically neuro-stimulating at least one nerve in a target body part by inducing an electric current between stimulation electrode 122 and dual-function electrode 126, essentially as described above in the description of FIG. 2.

Monitoring unit 334 is configured to transmit/send measurement data, e.g. measured potential differences, to control unit 310. In some embodiments, control unit 310 is configured to process the measurement data to obtain the values of the monitored heart parameters (e.g. heart-rate, HRV) and the stimulation parameters for an ensuing/follow-up neuromodulation. In some embodiments, the processing of the measurement data is performed on an external agent, as described in the description of module 100, method 200, and further elaborated on below. In some embodiments, monitoring unit 334 is configured to perform an ECG on a user of module 300.

Stimulation unit 338 is configured to generate an electric signal (e.g. a voltage signal or an electric current signal) between stimulation electrode 122 and dual-function electrode 126, in the second mode of operation. Stimulation unit 338 is further configured to obtain commands, e.g. stimulation parameters, from control unit 310. The stimulation parameters may specify the time-dependence of the generated electric signals.

In particular, in some embodiments, stimulation unit 338 is configured to automatically adjust the voltage and frequency applied between stimulation electrode 122 and dual-function electrode 126, such as to achieve a desired current amplitude and/or maximum intensity. As used herein, "maximum intensity" of a stimulation signal refers to the greater between the highest peak and the absolute value of the lowest trough thereof.

Stimulation unit 338 may include, for example, an AC current source or an electric signal generator, such that an intensity, a frequency, and a waveform of the voltage/current generated by stimulation unit 338 (including parameters characterizing a voltage/current including a continuous voltage/current pulse, intermittent voltage/current pulses, and burst modes) may be controllably varied in accordance with the stimulation parameters, thereby effecting neuromodulation of at least one nerve in a target body part as described above and in the description of FIG. 2.

Communication unit 320 is configured to send information to, and/or receive information from, an external agent, such as a smartphone, smartwatch, smart-band, a tablet, and/or a personal computer. The sending and the receiving of information (e.g. monitored heart parameters, determined stimulation parameters) may be implemented wirelessly and/or by wire. Communication unit 320 may be configured for long-distance communication (e.g. to a user's cloud storage, a user's personal computer, a computer system of the user's healthcare provider, and/or a personal computer of the user's physician/caregiver), by means of cellular networks, and/or Wi-Fi. Alternatively or additionally, communication unit 320 may be configured for short-range communication (e.g. to the user's smartphone or tablet), for example, by means of Bluetooth, NFC (near field communication) technology, and/or Wi-Fi.

In particular, in some embodiments, communication unit 320 may be used to relay information from control unit 310 to a user's smartphone/smartwatch and to relay commands from the user's smartphone/smartwatch to control unit 310, thereby facilitating controlling and operating module 300 by means of the smartphone/smartwatch.

In some such embodiments, the processing of monitoring unit 334 measurement data in step 230 to determine the values of the monitored heart parameters, and the determination of the stimulation parameters in step 240, may be carried out on an external agent, such as the user's smartphone. In some such embodiments, control unit 310 does not include a processor, thereby reducing the number of components in control unit 310 and the size of control unit 310, and consequently the size of module 300.

Figure 4A:
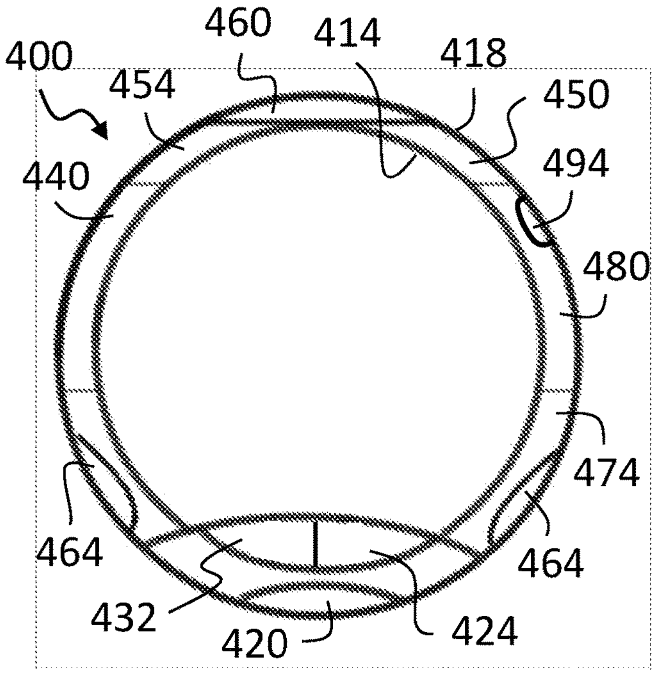
FIG. 4*a* schematically depicts a wearable element embodiment of the disclosure, configured to be worn about a wrist of a user, according to some embodiments.
Figure 4C:
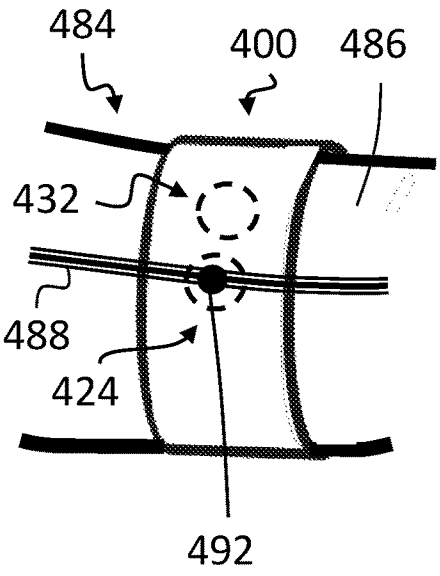
FIG. 4*c* schematically depicts the wearable element of FIG. 4*a*, worn about the wrist of the user, according to some embodiments.
Figure 4B:
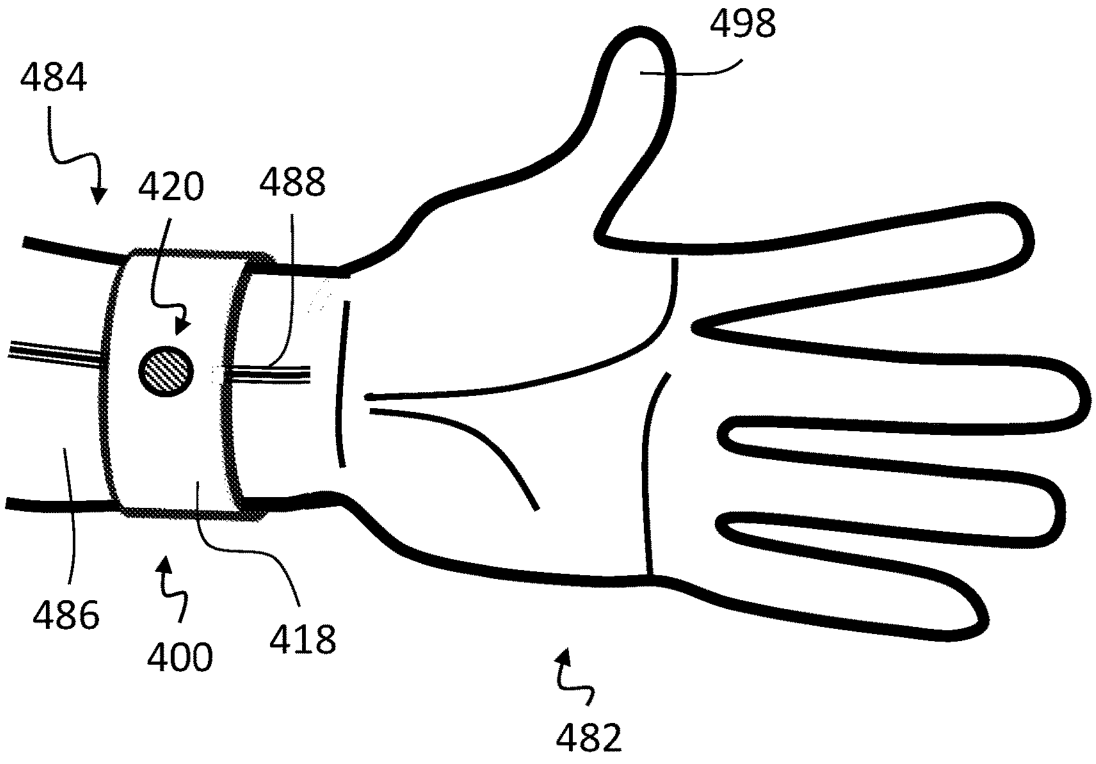
FIG. 4*b* schematically depicts the wearable element of FIG. 4*a*, worn about the wrist of the user, according to some embodiments.

Another embodiment of the disclosure is schematically depicted in FIGS. 4*a*-4*c*. FIGS. 4*a*-4*c* schematically depict a wearable element 400 (that is to say a wearable device), according to some embodiments. Wearable element 400 provides an example embodiment of module 100 and is configured to be worn about a wrist, an arm or a forearm (and in some embodiments, a neck or a leg) of a user and to effect neuromodulation of the median nerve in the wrist. In some embodiments, wearable element 400 is shaped as a band or a bracelet.

As shown in FIG. 4*a*, wearable element 400 includes an inner surface 414 extending along an inner circumference (not numbered) of wearable element 400, and an outer surface 418 extending along an outer circumference (not numbered) of wearable element 400. Wearable element 400 may further include a fastener/clasp (not shown) facilitating tightening and loosening of wearable element 400 about the wrist, placement of wearable element 400 thereon, and removal of wearable element 400 therefrom. In some embodiments, wherein wearable element 400, is shaped as a band, the band may be elastic. In some such embodiments, wearable element 400 does not include a fastener.

A monitoring electrode, monitoring cathode 420, is embedded in/on outer surface 418, such that an external surface of monitoring cathode 420 is exposed. A dual-function electrode, dual-function anode 424, is embedded in/on inner surface 414, such that an external surface of dual-function anode 424 is exposed, and is located opposite monitoring cathode 420. A stimulation electrode, stimulation cathode 432, is embedded in/on inner surface 414, such that an external surface of stimulation cathode 432 is exposed. In some embodiments, dual-function anode 424 and stimulation cathode 432 protrude from inner surface 414, and/or monitoring cathode 420 protrudes from outer surface 418.

Wearable element 400 further includes a stimulation unit 440 (i.e. an electrical stimulation inducing unit), a monitoring unit 450, a timer 454, a display 460 including a graphical user interface such as a touch screen, a communication unit 474, and a battery 480.

In some embodiments, wearable element 400 further includes one or more knobs 464464 (e.g. buttons). In some embodiments, display 460 does not include a touchscreen, and knobs 464 are used to control wearable element 400 operation. In some embodiments, wearable element 400 further includes a charger socket 494 for charging battery 480. In some embodiments, battery 480 may be charged wirelessly, and may also be removable.

It is noted that the positioning of above-numbered components (e.g. monitoring unit 450, timer 454) within wearable element 400, is exemplary, and other positionings of the components, within wearable element 400, may apply.

FIG. 4*b* schematically depicts wearable element 400 fastened about a wrist 484, according to some embodiments, from a side perspective, wherein a wrist inner part 486 is visible (that is to say, the inner part of wrist 484). Further depicted is a hand 482 (adjoining wrist 484), such that a palm (not numbered) of hand 482 is visible. A median nerve 488 extends along wrist 484 away from hand 482.

FIG. 4*c* presents an enlarged view of a portion of FIG. 4*b* including wrist 484 and wearable element 400. Monitoring cathode 420 is not shown. Being exposed only on inner surface 414, dual-function anode 424 and stimulation cathode 432 are not visible when wearable element 400 is worn, and as such each is schematically depicted by an empty circle delineated by a dashed line (as opposed to the pattern-filled circles used in FIGS. 1*a*-1*c* and in FIG. 4*b* to depict visible electrodes). Wearable element 400 may be sufficiently tightly fastened about wrist 484 such that dual-function anode 424 and stimulation cathode 432 are both in dermal contact with wrist inner part 486, with dual-function anode 424 being located proximately to median nerve 488, in wrist 484. Stimulation cathode 432 may be located closer to the thumb 498 of hand 482 than dual-function anode 424.

Wearable element 400 is operated substantially as described in FIG. 2. In the monitoring mode, the user, for example, places an opposing finger (e.g. a right finger when wearable element 400 is worn about the left wrist, as depicted in FIG. 4*b*) on monitoring cathode 420 and temporal fluctuations in the voltage between monitoring cathode 420 and dual-function anode 424, are monitored, thereby effecting a heart-rate measurement, as elaborated on below and in the description of FIG. 2.

Monitoring unit 450 is associated with stimulation unit 440, with timer 454, with knobs 464, with communication unit 474, with battery 480, and/or with other components. In the monitoring mode (i.e. the first mode), monitoring unit 450 is electrically associated with both monitoring cathode 420 and dual-function anode 424, which is electrically dissociated from stimulation cathode 432. Monitoring unit 450 includes a voltmeter (not shown), and is configured to monitor (continuously measure or intermittently measure) the potential difference between monitoring cathode 420 and dual-function anode 424 in the monitoring mode (e.g. in step 230), thereby effecting a heart-rate measurement, which enables projections/calculations of heart parameters (and/or obtaining an ECG/HRV reading), as elaborated on in the description of FIG. 2.

The values of the monitored heart parameters may be saved, dated, logged, and catalogued, thereby facilitating comparison between heart parameters obtained at different times and in different conditions, e.g. at rest, after a physical workout, and after a treatment provided in the second mode of operation. In some embodiments, the projection/calculations are performed by an external agent communicatively associated with wearable element 400. In some embodiments, wherein monitoring unit 450 further includes a computational unit, including a processor and a memory (all not shown), the projection/calculations may be performed by the computational unit.

Stimulation unit 440 is associated with monitoring unit 450, with timer 454, with knobs 464, with communication unit 474, with battery 480, and/or with other components. In the stimulation mode (i.e. the second mode), stimulation unit 440 is electrically associated with both stimulation cathode 432 and dual-function anode 424, which is electrically dissociated from monitoring cathode 420. (Dual-function anode 424 and stimulation cathode 432 are configured to have opposite polarities in the stimulation mode.) Stimulation unit 440 includes an electric signal generator, which may include an electric power source, such an AC or a DC current source, or be powered by battery 480. Stimulation unit 440 is configured to generate electric stimulation signals in the stimulation mode. Stimulation parameters (characterizing the stimulation signal), determined based on the values of the monitored heart parameters (e.g. in step 240), may be used by stimulation unit 440 to effect neuromodulation of median nerve 488. The neuromodulation is effected by conducting a current through a conduction pathway including dual-function anode 424, stimulation cathode 432, and a region near, or including (possibly partially), a segment of median nerve 488. It is noted that the electrical neuro-stimulation, provided in the second mode of operation, is local in the sense that the conduction pathway, and the current induced, are substantially restricted to the inner part of wrist 484. This local electrical stimulation of median nerve 488 may affect neurohormonal balance and autonomic nervous system control and consequently bring about a secretion of neural stimulation related hormones, and a decrease in secretion of stress related hormones, thereby affecting heart-rate, heart rhythm, HRV, and/or mood. Controllable electrical stimulation of median nerve 488 may thus allow for an indirect controllable influencing of heart-rate and HRV using non-intrusive electrodes (i.e. dual-function anode 424 and stimulation cathode 432).

In some embodiments, communication unit 474 is associated with stimulation unit 440, monitoring unit 450, and/or timer 454. Similarly to communication unit 320, in some embodiments, communication unit 474 is configured to transmit information to, and to receive information from, one or more external agents. The external agents may be used to perform some or all of the data processing and/or to control wearable element 400, essentially as described above and in the descriptions of method 200 and module 300.

In some embodiments, timer 454 may be configured to provide temporal information that may be used for operations related to the duration of a stimulation and/or monitoring session, or the duration of stimulation pulses and the duration of time intervals between successive stimulation pulses, and so on.

Display 460 is configured to display heart parameters obtained in the first mode of operation. In some embodiments, knobs 464 are configured to facilitate selecting one or more heart function parameters to be displayed, or one or more of a group of same heart function parameters obtained in different measurements, thereby facilitating a comparison of heart function in different times and conditions. Display 460 may also be configured to display heart function parameters during the first mode of operation. For example, display 460 may display a real-time or near real-time ECG reading of the user's heart.

In some embodiments, not exemplified in FIG. 4*a*, wearable element 400 does not include display 460, or any type of display. Values of monitored heart parameters, may be displayed on the user's smartphone, and/or on other external devices, such as a smartwatch, a tablet, and/or the like, which may receive information (e.g. by Wi-Fi, NFC, and/or Bluetooth) from wearable element 400.

In some embodiments, wearable element 400 may be partially or fully controlled (e.g. switched on and off, made to start or stop monitoring) via an external agent(s), such as a smartphone and/or a smartwatch. In some embodiments, wearable element 400 does not include knobs 464, or any other type of user interface, and may only be controlled via the external agent(s).

In some embodiments, wearable element 400 is configured to be worn about the left wrist of a user. In some embodiments, wearable element 400 may be worn about both the left wrist and the right wrist of a user (and may be used to electrically stimulate respective nerves therein).

FIG. 5*a*-5*b* depict results of monitoring heart parameters before and after treatment using a second-generation model of the wearable element of FIG. 4*a* on a single subject. Before the stimulation treatment, as shown in FIG. 5*a*, the SSDN parameter was 37.69, the rMSSD parameter was 26.46, and the heart rate was 73 bpm. After the stimulation session, as shown in FIG. 5*b*, the SSDN parameter was 71.58, the rMSSD parameter was 48.93, and the heart rate was 63 bpm, indicating a significant improvement in both the HRV related parameters, and the heart-rate.

Figure 5C:
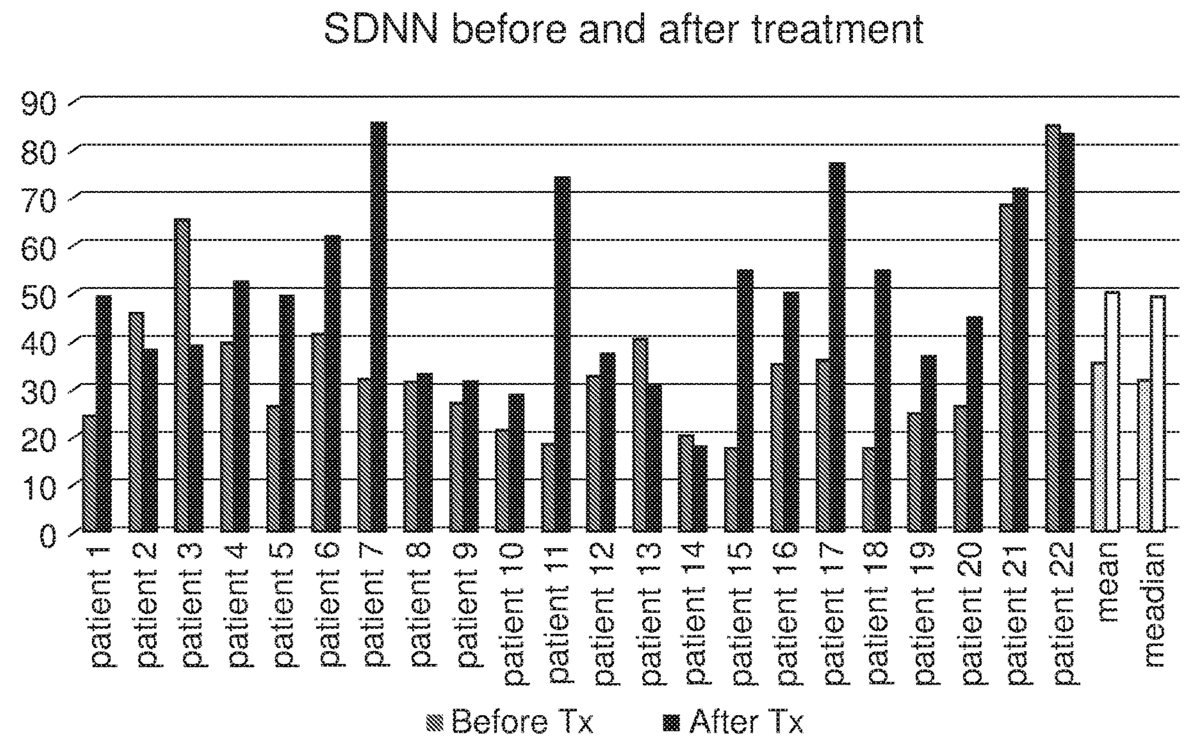
FIGS. 5*c*-5*e* depict results of monitoring and treatment using the second generation model of the wearable element of FIG. 4*a* on a group of 22 subjects.
Figure 5D:
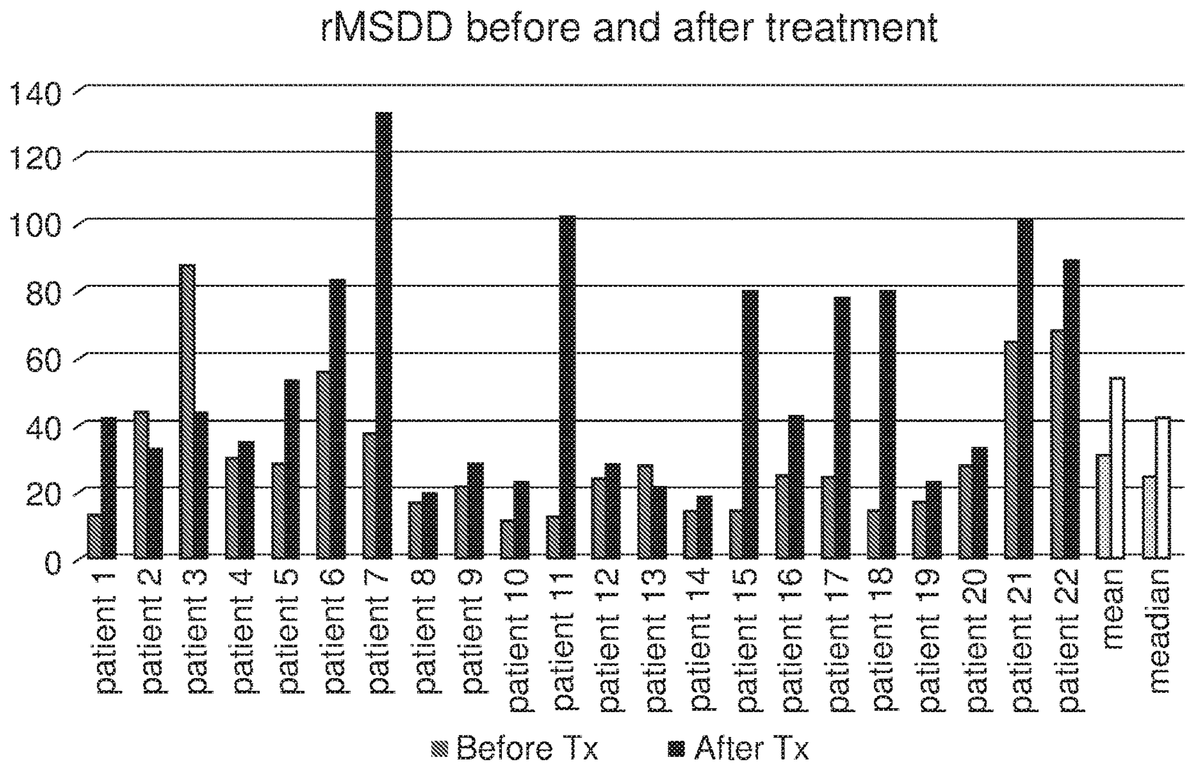
Figure 5E:
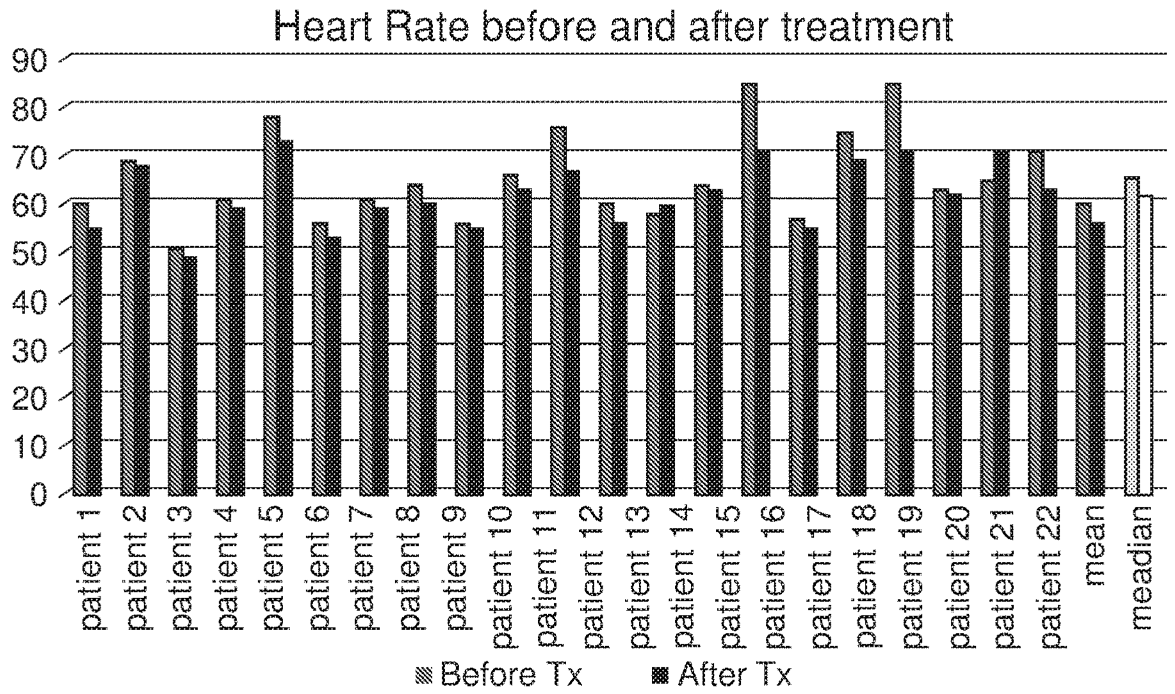

FIGS. 5*c*-5*e* depict results of monitoring and treatment using the second generation model of the wearable element of FIG. 4*a* on a group of 22 subjects. FIG. 5*c*, shows that the SSDN parameters of the 22 participants as it improved in average significantly before and after the stimulation session. FIG. 5*d*, shows that the rMSDD parameters of the 22 participants as it improved in average significantly before and after the stimulation session. FIG. 5*d*, shows that the heart rate of the 22 participants as it improved in average significantly before and after the stimulation session.

The summary of data depicted in FIGS. 5*c*-5*e* is presented in the following table:

| | Mean(SD) before | Mean(SD) after | Delta mean | % change | P value | % of persons with change |
|---|---|---|---|---|---|---|
| SDNN | 35.4(17) | 50.19(19) | 14.78954545 | 41.77354954 | p = 0.003 | 17 of 22 = 77.2% |
| rMSSD | 31.11(20) | 54.28(33) | 23.17 | 74.47 | p = 0.0038 | 19 of 22 = 86.3% |
| HR | 65.5 | 61.72727273 | −3.772727273 | −5.759888966 | P = 0.0008 | 21 of 22 = 95.4% |

Figure 5F:
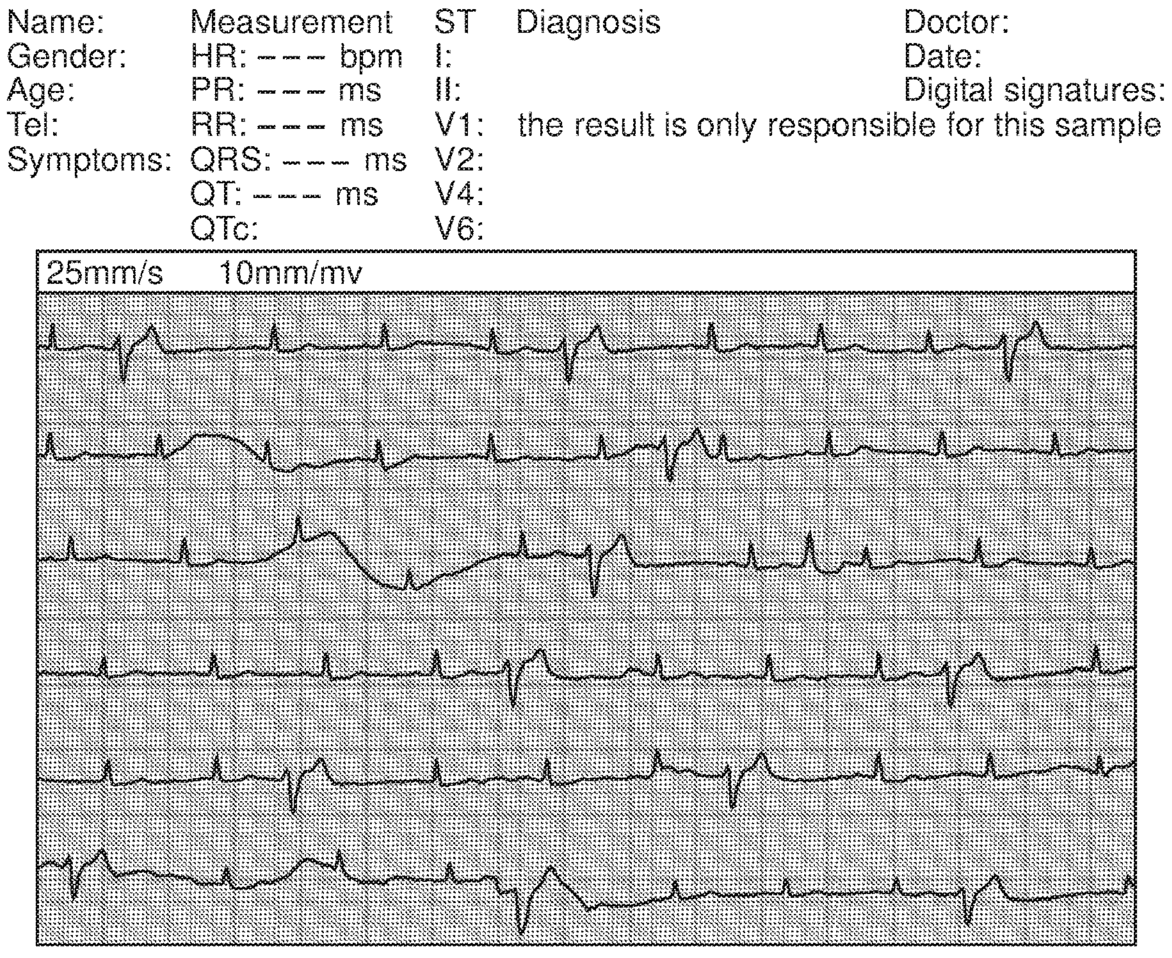
FIG. 5*f*-5*g* depict results of ECG recording before and after treatment using a second-generation model of the wearable element of FIG. 4*a* on a single subject.
Figure 5G:
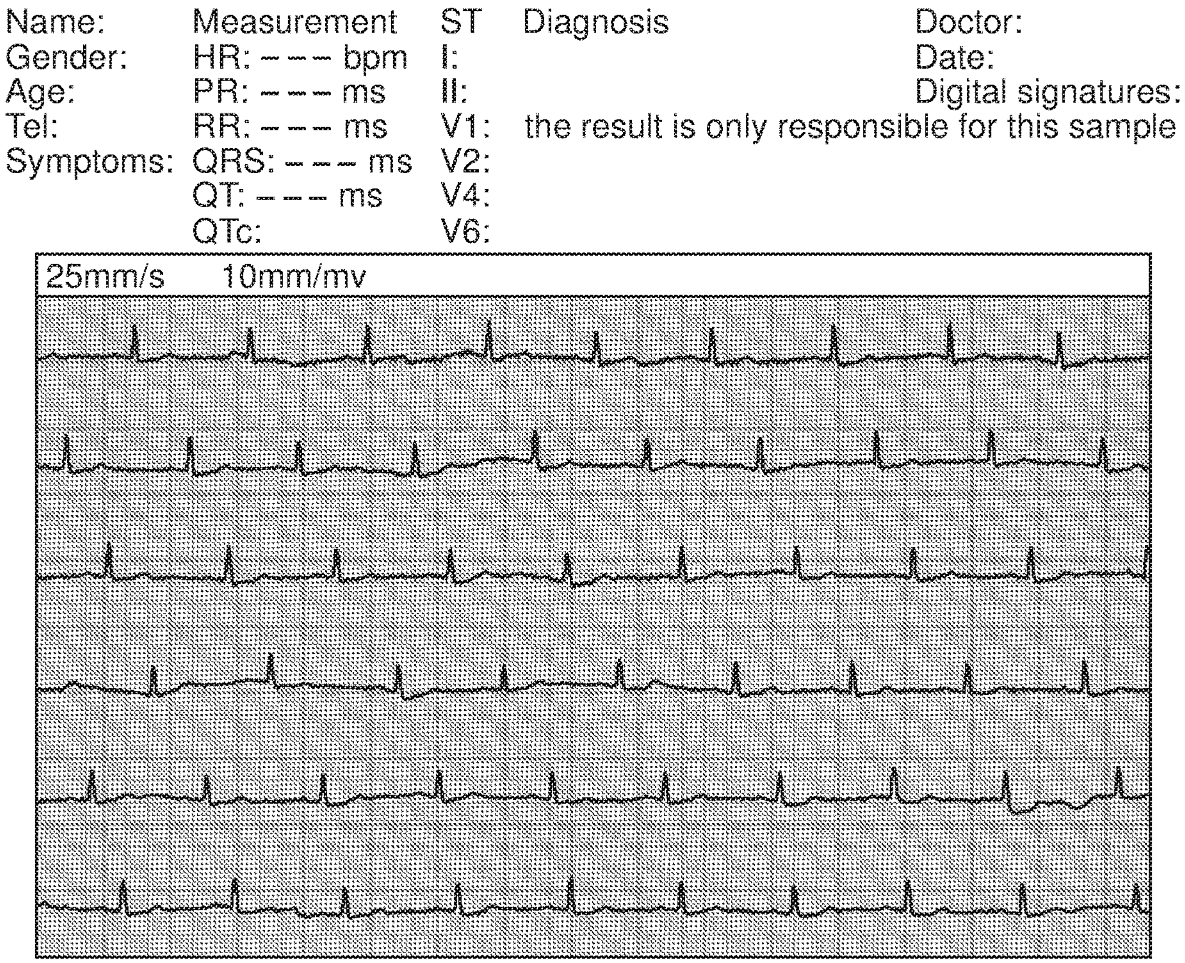

FIG. 5*f*-5*g* depict results of ECG recording before and after treatment using a second-generation model of the wearable element of FIG. 4*a* on a single subject. In FIG. 5*f*, arrhythmias of the heart can be notices very clearly, the total heart beats over 5 minutes reached 326 beats, the total VPC's in those five minutes were 42 (amounting for 12.8% of the total heart beats), and the average heart-rate was 65 bpm. After the stimulation session, as depicted in FIG. 5*g*, the arrhythmia improved dramatically as the total heart beats over 5 minutes were 300 beats, and the total VPC's in those 5 minutes were 8 (amounting for 2.6% of the total heart beats), with the average heart rate being 60 bpm.

It is noted that SDNN, rMSSD, pNN50, and LF/HF, are different parameters used in the art to analyze HRV. Low HRV, as quantified by low readings of the above parameters, is considered, as mentioned above, to indicate poor communications and control of the autonomic nervous system over the cardiovascular system. Correlates of low HRV may indicate poor cardiovascular health, a high stress state, poor sleep or poor physical recovery abilities. The results of the experiments thus show marked improvements in HRV following the treatments, emphasizing some potential benefits of the disclosed embodiments for the conditions above.

A study to assess the efficacy and effect of treatment using a second generation model of the wearable element of FIG. 4*a* has been conducted, and the results thereof are provided in the following table, and corresponding FIG. 6.

| HRV specific protocols (n = 52 treatments) | Group Mean(SD) before | Group Mean(SD) after | Delta mean | Delta SD | mean % change | paired t-test | Sample Size (treatments) 0.8 | Sample Size (treatments) 0.9 |
|---|---|---|---|---|---|---|---|---|
| SDNN | 34.63(19) | 43.61(19) | 8.98 | 16.19 | 26% | P = 0.000086623193 | 41 | 57 |
| rMSSD | 29.31(21) | 42.47(32) | 13.17 | 26.18 | 44.9% | P = 0.00032395315 | 50 | 69 |
| HR | 68.1(14) | 64.89(13) | −3.2 | 4.74 | −4.69% | P = 0.00000336007 | 28 | 39 |

Figure 6:
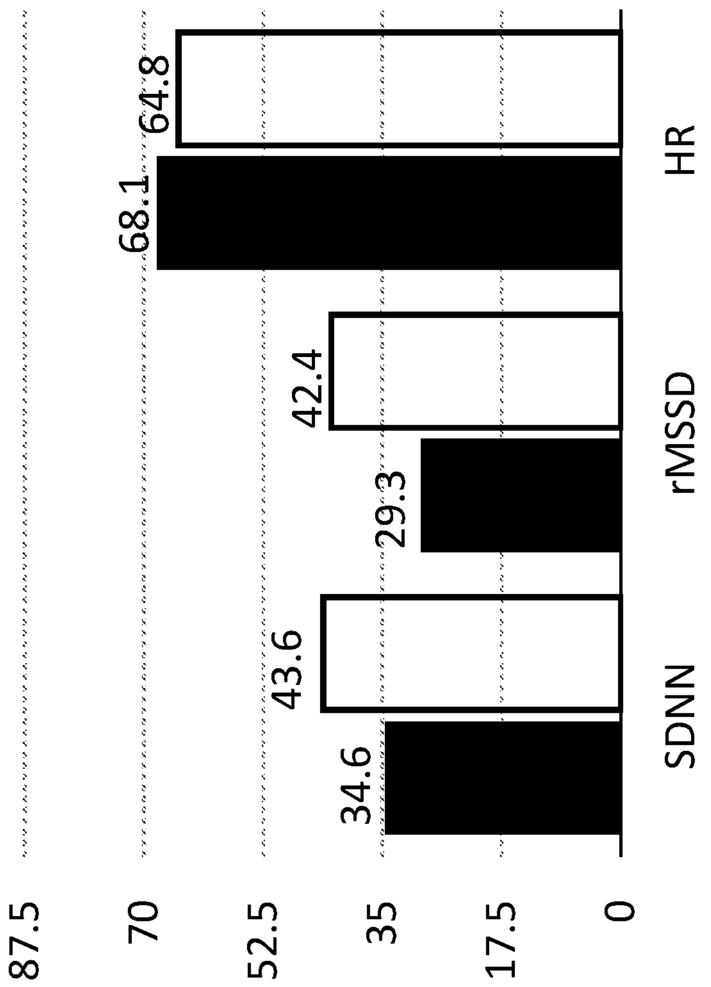
FIG. 6 schematically depicts results of monitoring and treatment using a second generation model of the wearable element of FIG. 4*a* on a group of 52 subjects.

FIG. 6 schematically depicts results, which show an improvement of the group average SDNN from 34.6 before the treatment, to 43.6 after the treatment; and an improvement in the rMSSD from 29.3 in group average before the treatment, to 42.4 after the treatment.

Decreasing heart rate is part of arrhythmia treatment strategy in cardiology involving rate control and rhythm control. The results also show decreased heart rate of close to 5% which may signify deceased susceptibility to arrhythmias and also decreased heart rate recovery time in athletes.

In some embodiments, a module or wearable element, such as wearable element 400 (and modules 100 and 300), may be used as a fitness device. HRV data obtained in the monitoring mode may be used to determine physical readiness prior to a (physical) workout session and help establish an improved workout session plan. In addition, HRV data obtained from repeated monitorings over an extended period (e.g. days, weeks, or months) may be used to monitor/evaluate progress in fitness, and to provide adjustments to the workout plan, and/or to treatment administered (i.e. neuromodulation administered using the devices and methods disclosed herein) prior, during, and/or after a workout session, could be made accordingly. Moreover, one aspect of the disclosure, i.e. neuromodulation capabilities, may directly enhance physical performance and recovery in a workout session by improving HRV parameters. A trainer could thus use the module for both monitoring before, during, and after training and for improving performance in training.

An example workout session, based on monitoring, as well as treatment, according to some embodiments of the devices and methods disclosed herein, may include some or all of the following steps:

Putting on the module on the wrist and selecting the monitoring mode.

Measuring HRV, as described above.

Selecting the stimulation mode, and deciding on a workout session goal (e.g. mild, moderate, intense, and/or aerobic or strength and resistance training, and so on). The workout session goal may be determined taking into account the HRV reading The module, or an external agent in communication with the module, may automatically determine the values of the stimulation parameters according to the data acquired in the monitoring mode and according to the workout session goal. For example, a processing unit algorithm may be programmed to output low frequency stimulation (0.5-5 Hz) or high frequency stimulation (for example 100 Hz) according do monitored acquired data parameters and desired session or treatment goals. Other monitoring and stimulation parameters could also be utilized. Alternately, a trainer may manually select the stimulation parameters.

The module may automatically switch between the stimulation mode and the monitoring mode, so that periods of stimulation may by followed by periods of monitoring, to obtain updated HRV readings. The module may automatically adjust the values of the stimulation parameters according to the updated HRV readings.

When the training session is completed, low frequency stimulation for optimizing fitness recovery may be manually selected or automatically suggested and performed by the module.

Optionally, the stimulation parameters may be provided by a cloud server or an external compute unit, configured to determine the stimulation parameters based on data analysis related to other users and/or previous stimulations and measurements.

Figure 7A:
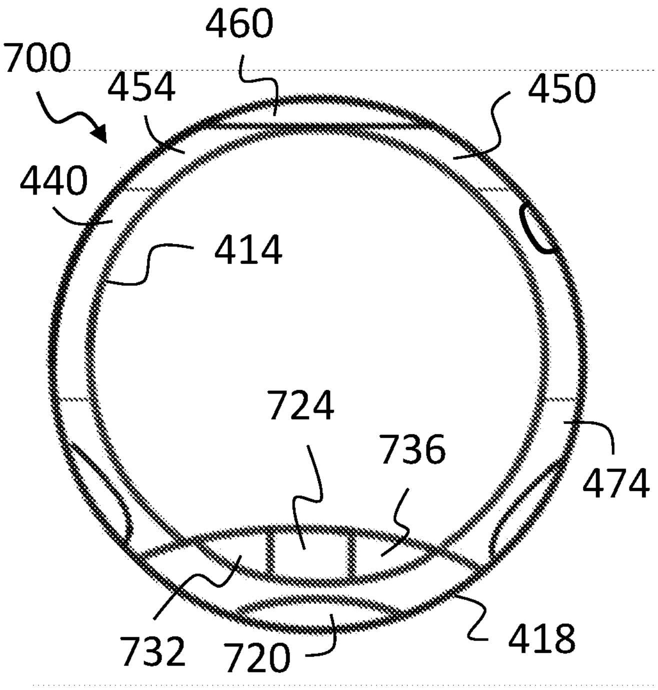
FIG. 7*a* schematically depicts a wearable element embodiment of the disclosure, configured to be worn about a wrist of a user, according to some embodiments.
Figure 7B:
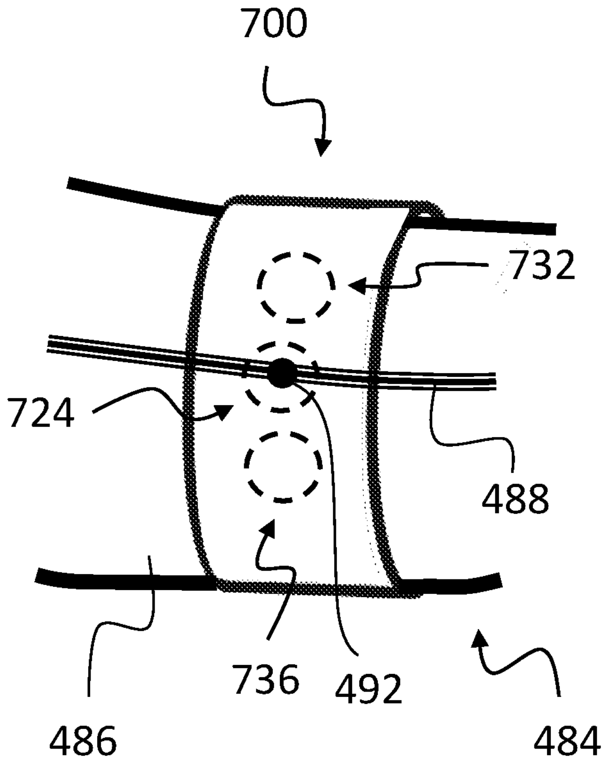
FIG. 7*b* schematically depicts the wearable element of FIG. 7*a*, worn about the wrist of the user, according to some embodiments.

Another embodiment of the disclosure is schematically depicted in FIGS. 7*a*-7*c*. FIG. 7*a* depicts a wearable element 700, according to some embodiments. Wearable element 700 provides an example embodiment of module 100. Wearable element 700 is essentially similar to wearable element 400, but differs in further including an additional stimulation cathode. To distinguish electrodes in wearable element 700 from corresponding electrodes in wearable element 400, all electrodes in wearable element 700 are assigned new numbers, while all other elements in wearable element 700 retain the numbers of the respective counterparts thereof in wearable element 400.

Wearable element 700 includes a monitoring cathode 720, a dual-function anode 724, a first stimulation cathode 732, and a second stimulation cathode 736. Monitoring cathode 720 is embedded in/on outer surface 418. Dual-function anode 724 is embedded in/on inner surface 414, opposite to monitoring cathode 720. First stimulation cathode 732 and second stimulation cathode 736 are embedded in/on inner surface 414. First stimulation cathode 732, dual-function anode 724, and second stimulation cathode 736 are sequentially arranged along the inner circumference of wearable element 700. That is to say, dual-function anode 724 is located between first stimulation cathode 732 and second stimulation cathode 736, with first stimulation cathode 732 being located closest to thumb 498. Respective external surfaces (not numbered) of all the electrodes are exposed.

In some embodiments, the association between elements in wearable element 700 is identical to that of the respective counterparts thereof in wearable element 400, apart from extra associations involving second stimulation cathode 736 (which has not counterpart in wearable element 400), as elaborated on below.

FIG. 7*b* schematically depicts a view of an inner part of wrist 484 with wearable element 700 wore thereon, according to some embodiments. Being exposed only on inner surface 414, dual-function anode 724 and stimulation cathodes 732 and 736 are not visible when wearable element 700 is worn, and as such each is schematically depicted by an empty circle delineated by a dashed line. Monitoring cathode 720 is not shown, but is understood to be positioned in/on outer surface 418 opposite dual-function anode 724 (essentially similarly to monitoring cathode 420 in FIG. 4*b*). Wearable element 700 is configured to facilitate sufficiently tight fastening about wrist 484 such that dual-function anode 724 and stimulation cathodes 732 and 736 are all simultaneously in dermal contact with wrist inner part 486, with dual-function anode 724 being located proximately to median nerve 488. The first mode of operation of wearable element 700 is essentially similar to the first mode of operation of wearable element 400, with monitoring cathode 720 and dual-function anode 724 playing analogous roles to monitoring cathode 420 and dual-function anode 424, respectively.

The second mode of operation of wearable element 700 is similar to the second mode of operation of wearable element 400, but differs in that three electrodes, instead of two, are used for the neuromodulation; the electrodes being dual-function anode 724 and stimulation cathodes 732 and 736. Neuromodulation of median nerve 488 is effected by simultaneously closing two conduction pathways. A first conduction pathway (which is similar to the conduction pathway closed in the second mode of operation of wearable element 400) passes through dual-function anode 724, first stimulation cathode 732, and a first region near, or including (possibly partially), a first segment of median nerve 488. A second conduction pathway passes through dual-function anode 724 and second stimulation cathode 736, and a second region near, or including (possibly partially), a second segment of median nerve 488. In some embodiments, the first segment and second segment of median nerve 488 are the same.

Further modes of operation may apply. For example, a mode of operation may include iterative stimulation by altering the utilization of stimulation cathodes 732 and 736 for compensating for a misplacement of wearable element 700 around the wrist, relative to the median nerve.

It is noted that the presence of a second stimulation cathode (second stimulation cathode 736) may facilitate, in the stimulation mode, conducing through dual-function anode 724 a greater current than the maximum current which can conveniently/safely be conducted through dual-function anode 424, due to the combined surface area of stimulation cathodes 732 and 736 being potentially greater than that of stimulation cathode 432.

In some embodiments, first stimulation cathode 732 is also dual-functional. In the stimulation mode first stimulation cathode 732 function remains unchanged (that is to say, first stimulation cathode 732 functions as described above). In the monitoring mode, however, first stimulation cathode 732 is no longer passive and acts as a monitoring electrode. More specifically, in the monitoring mode, first stimulation cathode 732 and dual-function anode 724 are electrically associated such as to form a substantially equi-potential surface, thereby effectively acting as a single electrode. Monitoring of heart parameters is performed by monitoring temporal variations in the potential difference between monitoring cathode 720 and the substantially equi-potential surface formed by first stimulation cathode 732 and dual-function anode 724. The increased dermal contact provided by first stimulation cathode 732 may potentially allow for obtaining improved ECG readings.

Figure 8A:
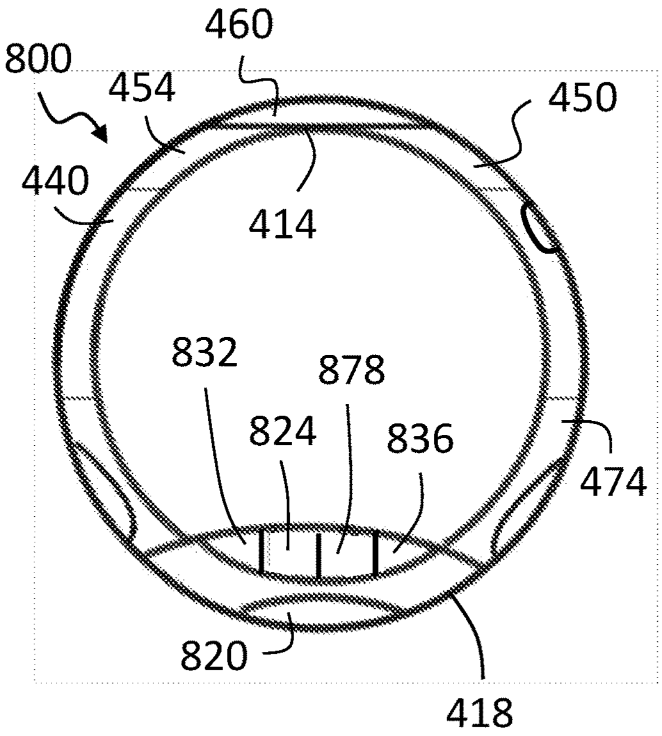
FIG. 8*a* schematically depicts a wearable element embodiment of the disclosure, configured to be worn about a wrist of a user, according to some embodiments.
Figure 8B:
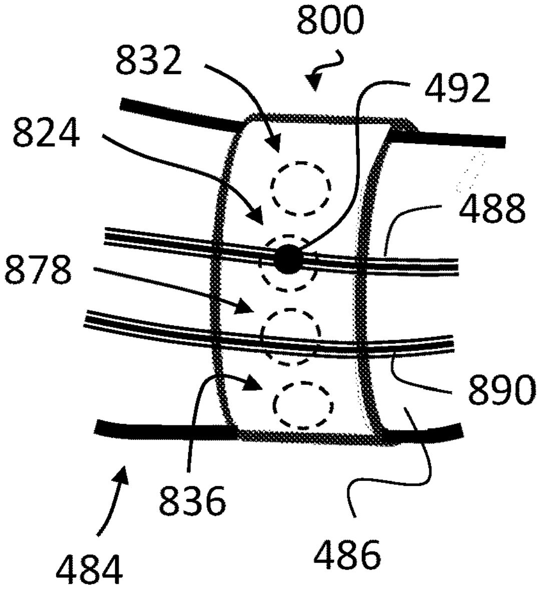
FIG. 8*b* schematically depicts the wearable element of FIG. 8*a*, worn about the wrist of the user, according to some embodiments.
Figure 9A:
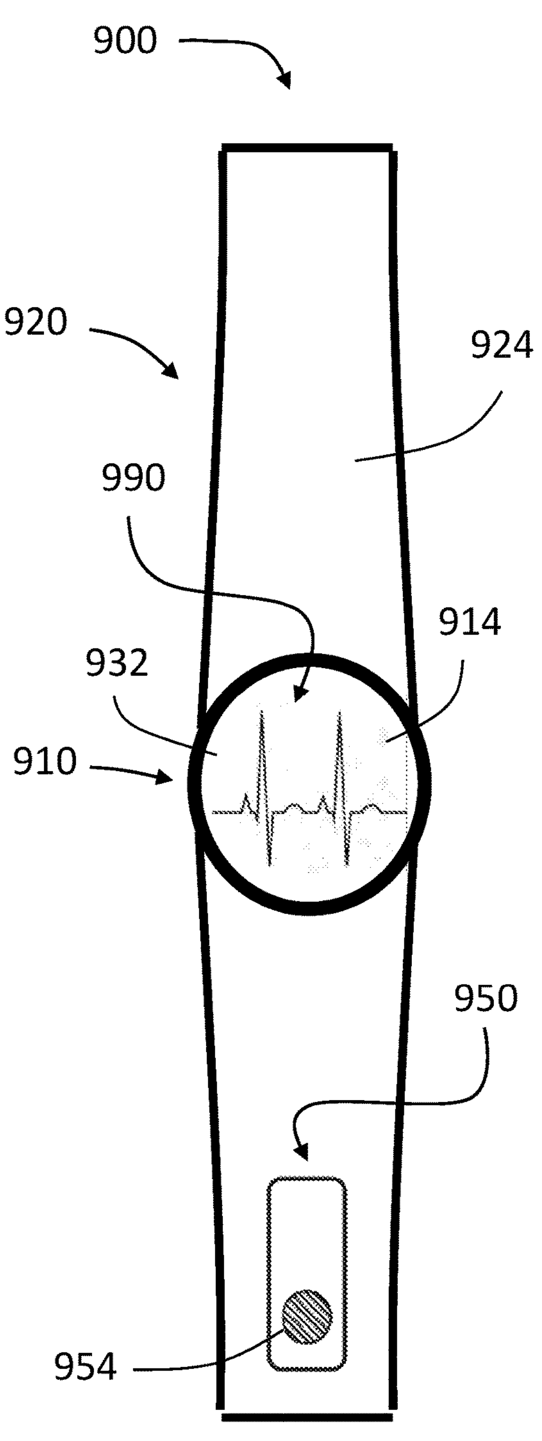
FIG. 9*a* schematically depicts a front-view of a smart-watch embodiment of the disclosure, according to some embodiments.
Figure 9B:
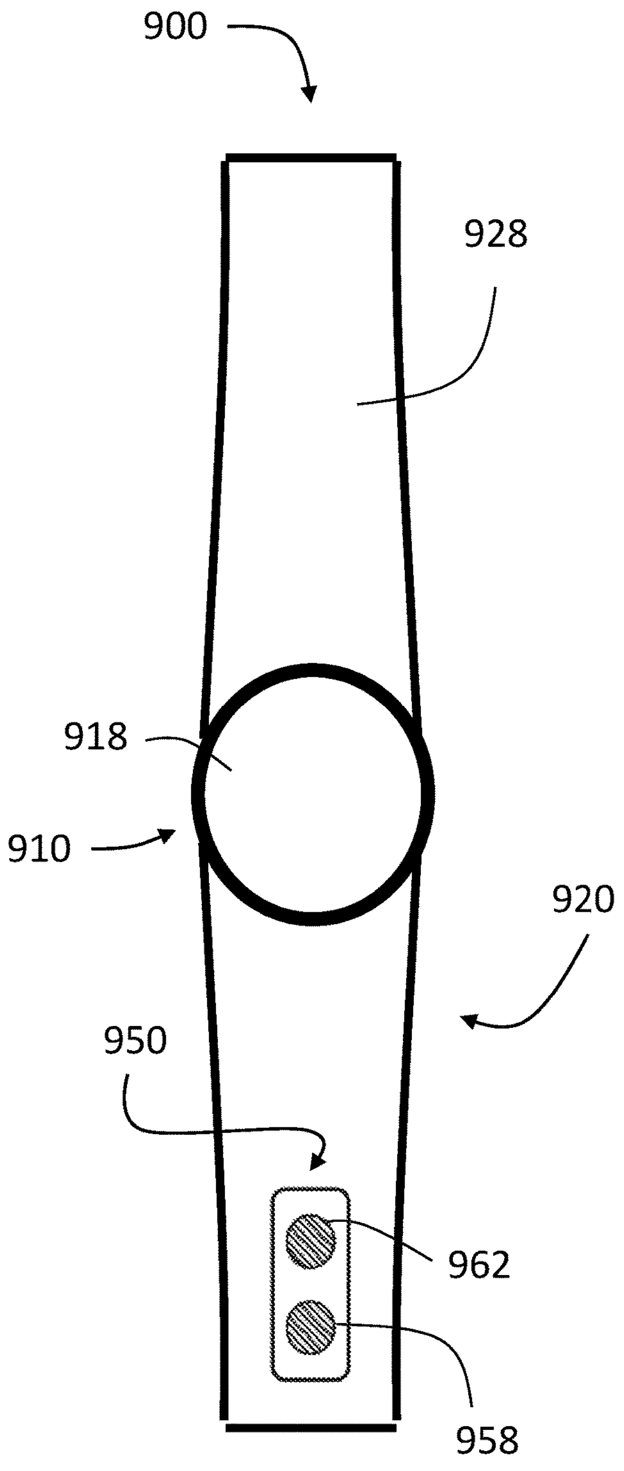
FIG. 9*b* schematically depicts a back-view of the smart-watch of FIG. 9*a*, according to some embodiments.

Another embodiment of the disclosure is schematically depicted in FIGS. 8*a*-8*c*. FIG. 8*a* depicts a wearable element 800 according to some embodiments. Wearable element 800 provides an example embodiment of module 100. Wearable element 800 is essentially similar to wearable element 700, but differs in further including an additional anode, and optionally in the spatial arrangement of the electrodes, as elaborated on below. To distinguish electrodes in wearable element 800 from corresponding electrodes in wearable element 700, all electrodes in wearable element 800 are assigned a new numbers, while all other elements in wearable element 800 retain the numbers of the respective counterparts thereof in wearable element 700.

Wearable element 800 includes a monitoring cathode 820, a dual-function anode 824, a first stimulation cathode 832, a second stimulation cathode 836, and a stimulation anode

878. Monitoring cathode 820 is embedded in/on outer surface 418. Dual-function anode 824 is embedded in/on inner surface 414, opposite to monitoring cathode 820. First stimulation cathode 832, second stimulation cathode 836, and stimulation anode 878, are embedded in/on inner surface 414. First stimulation cathode 832, dual-function anode 824, stimulation anode 878, and second stimulation cathode 836 are sequentially arranged along the inner circumference of wearable element 800. That is to say, dual-function anode 824 is located between first stimulation cathode 832 and stimulation anode 878, and stimulation anode 878 is located between dual-function anode 824 and second stimulation cathode 836, with first stimulation cathode 832 being located closest to thumb 498. Respective external surfaces (not numbered) of all the electrodes are exposed. In some embodiments, any one or more of the electrodes in/on the inner surface may be a dual-functional electrode.

In some embodiments, the association between elements in wearable element 800 is identical to that of the respective counterparts thereof in wearable element 700, apart from extra associations involving stimulation anode 878 (which has not counterpart in wearable element 700), as elaborated on below.

FIG. *8b* schematically depicts a view of an inner part of wrist 484 with wearable element 800 wore thereon, according to some embodiments. Being exposed only on inner surface 414, anodes 824 and 878 and cathodes 832 and 836 are not visible when wearable element 800 is worn, and as such each is schematically depicted by an empty circle delineated by a dashed line. Monitoring cathode 820 is not shown, but is understood to be positioned in/on outer surface 418, for example, opposite to dual-function anode 824 (essentially similarly to monitoring cathode 420 in FIG. *4b*). Wearable element 800 is configured to facilitate sufficiently tight fastening about wrist 484 such that anode 824 and 878, and cathodes 832 and 836, are all simultaneously in dermal contact with wrist inner part 486, with dual-function anode 824 being located proximately to median nerve 488, 492, and with stimulation anode 878 being located proximately to ulnar nerve 890. The first mode of operation of third wearable element 800 is essentially similar to the first mode of operation of wearable element 700, with monitoring cathode 820 and dual-function anode 824 playing analogous roles to monitoring cathode 720 and dual-function anode 724, respectively.

In some embodiments, in the second mode of operation of wearable element 800, both median nerve 488 and ulnar nerve 890 are simultaneously electrically stimulated. Neuromodulation of median nerve 488 may be effected by closing a first conduction pathway through dual-function anode 824, first stimulation cathode 832, and a first region near, or including (possibly partially), a segment of median nerve 488. Neuromodulation of ulnar nerve 890 may be effected by closing a second conduction pathway passing through stimulation anode 878, second stimulation cathode 836, and a second region near, or including (possibly partially), a segment of ulnar nerve 890.

Further modes of operation may apply. For example, only one of median nerves 488 and ulnar nerve 890 may selectively be neuromodulated, or median nerve 488 and ulnar nerve 890 may be alternately neuromodulated. Furthermore, a mode of operation may include iterative stimulation by altering the utilization of stimulation cathodes 832 and 836 for compensating for a misplacement of third wearable element 800.

In some embodiments, the arrangement of the electrodes on inner surface 414 may differ. In some embodiments, dual-function anode 824 is located between stimulation cathodes 832 and 836, and second stimulation cathode 836 is located between anodes 824 and stimulation anode 836, such that first stimulation cathode 832, dual-function anode 824, second stimulation cathode 836, and stimulation anode 878 are arranged sequentially along the inner circumference of third wearable element 800. Such an arrangement may be more suitable for a user having a broader wrist, and therefore having a larger separation of median nerve 488 and ulnar nerve 890.

In some embodiments, the roles of stimulation anode 878 and second stimulation cathode 836 may be controllably reversed. That is to say, wearable element 800 further includes a switch (not shown) allowing the user to controllably switch between a first configuration and a second configuration. In the first configuration, dual-function anode 824 and first stimulation cathode 832 function as described above. In the second configuration, the polarities of dual-function anode 824 and stimulation cathode 832 are reversed. Switching between the first configuration and the second configuration may compensate for variation in the separation (i.e. distance) between median nerve 488 and ulnar nerve 890 from one user to another. A user having a narrow wrist, and therefore a smaller separation between the nerves may want to select the first configuration. A user having a broad wrist, and therefore a larger separation between the nerves, may want to select the second configuration, wherein due to the larger separation between the nerves, second stimulation cathode 836 may be closer to ulnar nerve 890 than stimulation anode 878 (with dual-function anode 824 remaining closer to median nerve 488 than first stimulation cathode 832).

In some embodiments, stimulation anode 878 is also dual-functional, and similarly to dual-function anode 824, may be used both for stimulation and monitoring. Monitoring effected using both dual-function anode 824 and stimulation anode 878 may lead to an improved ECG signal as compared to monitoring effected using just one anode, due to an increase in anode external surface area in dermal contact with the wrist (i.e. combined external surface area of dual-function anode 824 and stimulation anode 878 as compared to external surface area of dual-function anode 424).

In some embodiments, wearable elements 400, 700, and 800 may be worn about a mid-part of a forearm or a proximal part of the forearm, such as to effect neuromodulation of the median nerve and/or the ulnar nerve in the forearm. In some embodiments, the wearable elements may be worn about an upper arm, such as to effect neuromodulation of the median nerve and/or the ulnar nerve in the upper arm. In some embodiments, the wearable elements may be elastic and may be adjusted to be worn about any part of the arm, such as to effect neuromdoulation as described above. In some embodiments, the wearable elements may be worn about a leg, for example, about the thigh, such as to induce neuromodulation of one or more peripheral nerves in the leg. In Some embodiments, wearable elements 400, 700, and 800 may be worn about a leg or a neck of a user, to effect neuromodulation of nerves therein.

Another embodiment of the disclosure is schematically depicted in FIGS. *9a-9b*. FIG. *9a* and FIG. *9b* schematically depict a front-view and a back-view of a smartwatch 900, respectively, according to some embodiments. Smartwatch 900 includes a watch body 910 having a front surface 914 and a back surface 918. Watch body 910 includes a computational unit—including a processor and a memory—and a battery (all not shown). Smartwatch 900 further includes a watch strap 920 having a strap outer surface 924 and a strap inner surface 928. Front surface 914 includes a watch user interface 932, e.g. a touchscreen (which also functions as a display).

Smartwatch 900 includes a smart module 950 embedded in watch strap 920. Smart module 950 provides an example embodiment of module 100. In some embodiments, smart module 950 is modular, in the sense of facilitating easy installation on, and removal from, a modular slot (not shown) on watch strap 920. In some embodiments, the modular slot is configured to accommodate different smart modules, thereby allowing a user to swap between smart modules as desired. Smart module 950 includes a monitoring electrode, monitoring cathode 954, on an outer surface (not numbered) thereof, and a dual-function electrode, dual-function anode 958, and a stimulation electrode, stimulation cathode 962, on an inner surface (not numbered) thereof. An external surface (not numbered) of monitoring cathode 954 is exposed on strap outer surface 924. An external surface (not numbered) of dual-function anode 958, and an external surface (not numbered) of stimulation cathode 962, are exposed on strap inner surface 928.

Smartwatch 900 is configured to be worn about a wrist of a user such that dual-function anode 958 is located proximately to the median nerve in the wrist, Watch strap 920 may be fastened and tightened, such as to establish dermal contact between the inner part of the wrist and dual-function anode 958 and stimulation cathode 962. In some embodiments, the wrist is a left wrist. Advantageously, stimulating of the left wrist may provide an enhanced stimulation effect as compared to stimulating the right wrist due to the anatomical physiological relations of the left median nerve to the vagus nerve.

Smart module 950 includes a control unit, a monitoring unit, and a stimulation unit (all not shown). The monitoring unit is associated with, and controlled by, the control unit, and is further associated with monitoring cathode 954 and selectively associated with dual-function anode 958. The stimulation unit is associated with, and controlled by, the control unit and is further selectively associated with dual-function anode 958, as well as being associated with stimulation cathode 962. The control unit is controlled by the computation unit in watch body 910 and is configured to send information to, and receive information from, the computational unit. Module 950 may thus be controlled through watch user interface 932. In particular, watch user interface may display heart parameters, and ECG readings (ECG reading 990).

In some embodiments, devices and methods disclosed herein may be used for prediction, prevention and treatment of cardiovascular pathologies. More specifically, repeated HR/HRV or ECG measurements, in the monitoring mode of the above-mentioned embodiments, may indicate to a user a deterioration of neuro-cardio balance and predict a cardiovascular event. For example, a sudden impairment of LF or LF/HF ratio may imply an upcoming onset of an atrial fibrillation (AF) episode for a patient with AF history. By operating the stimulation mode, HR and HRV parameters may improve, thus preventing the occurrence of the AF episode. In addition, scheduled preventative treatments may be utilized in the stimulation mode. Moreover, the above-mentioned embodiments may be used during an initial stage of a cardiac event, providing what may prove to be a crucial immediate basic treatment prior to a comprehensive treatment, e.g. in a hospital. The above-mentioned embodiments may also be used for improving cardiovascular parameters after a cardiovascular procedure or event. For example, decreased HRV parameters may be addressed after a myocardial infarct to improve long term survival, as mentioned by the EU and US cardiology societies (see hereinabove in the Summary). In addition, certain cardiovascular procedures may be followed by a scheduled stimulation regiment applied by the above-mentioned embodiments. For example, decreased HRV before and after ablation procedure of cardiac arrhythmias may be addressed, thus possibly improving outcomes of the procedures.

Cardiac arrhythmias such as VPBs (ventricular premature beats, also known as "ventricular premature contractions" (VPCs) (as demonstrated by the second generation prototype in FIGS. 5*a* and 5*b*, APBs (atrial premature beats, also known as "atrial premature complexes" (APCs), PAF (paroxysmal atrial fibrillation), CAF (chronic atrial fibrillation), PsAF (persistent atrial fibrillation), SVT (supraventricular tachycardia) and atrial tachycardia may benefit from the monitoring and stimulation capabilities of the above-mentioned embodiments. Other cardiovascular disorders such as decreased coronary blood flow, cardiac muscle contractile disorders (such as heart failure) and high blood may also be addressed.

In some embodiments of modules and wearable elements (such as modules 100 and 300, and wearable elements 400, 700, and 800, and smartwatch 900), the radius of the electrodes may range from approximately 1 mm to approximately 10 mm, and according to some embodiments, from approximately 4 mm to approximately 6 mm. The distance between adjacent electrodes having opposite polarities, respectively, as quantified via a distance between respective centers of adjacent electrodes (on the same surface, such as inner surface 114 or inner surface 414) may range from approximately 3 mm to approximately 30 mm, according to some embodiments, from approximately 15 mm to approximately 25 mm, or even from approximately 18 mm to approximately 22 mm. In some embodiments of modules and wearable elements (such as modules 100 and 300, and wearable elements 400, 700, and 800, and smartwatch 900), the electrodes have a radius of approximately 3-10 mm and the distance between adjacent electrodes, having opposite polarities may range from 10 to 20 mm.

In some embodiments the electrodes may be square, oval or any other ordinary or unordinary shape, having sizes and surfaces areas lying in ranges similar to above-mentioned ranges.

Dimensions of electrodes may vary according to a target body part on which the electrodes are to be placed. Thus, in some embodiments of modules and wearable elements (such as modules 100 and 300, and wearable elements 400, 700, and 800, and smartwatch 900), the sizes of and surface areas of the electrodes, and the distances between electrodes, may vary beyond the above-mentioned ranges.

In some embodiments of modules and wearable elements (such as modules 100 and 300, and wearable elements 400, 700, and 800, and smartwatch 900), the current(s) conducted via the conduction pathway(s) in the second mode of operation may range from 10 μA (i.e. micro-Ampere) to 5 A, and preferably from 100 μA to 500 mA (i.e. milli-Ampere). In a preferred embodiment, the current may from range 1 mA to 15 mA. The frequencies of the electrical stimulation signals used to neuromodulate the median and ulnar nerves may range from 0.05 Hz to 1000 Hz, and preferably from 0.25 Hz to 100 Hz. As used herein, the terms "smartwear" and "smart-band" may refer to a wearable electronic device.

Figure 10:
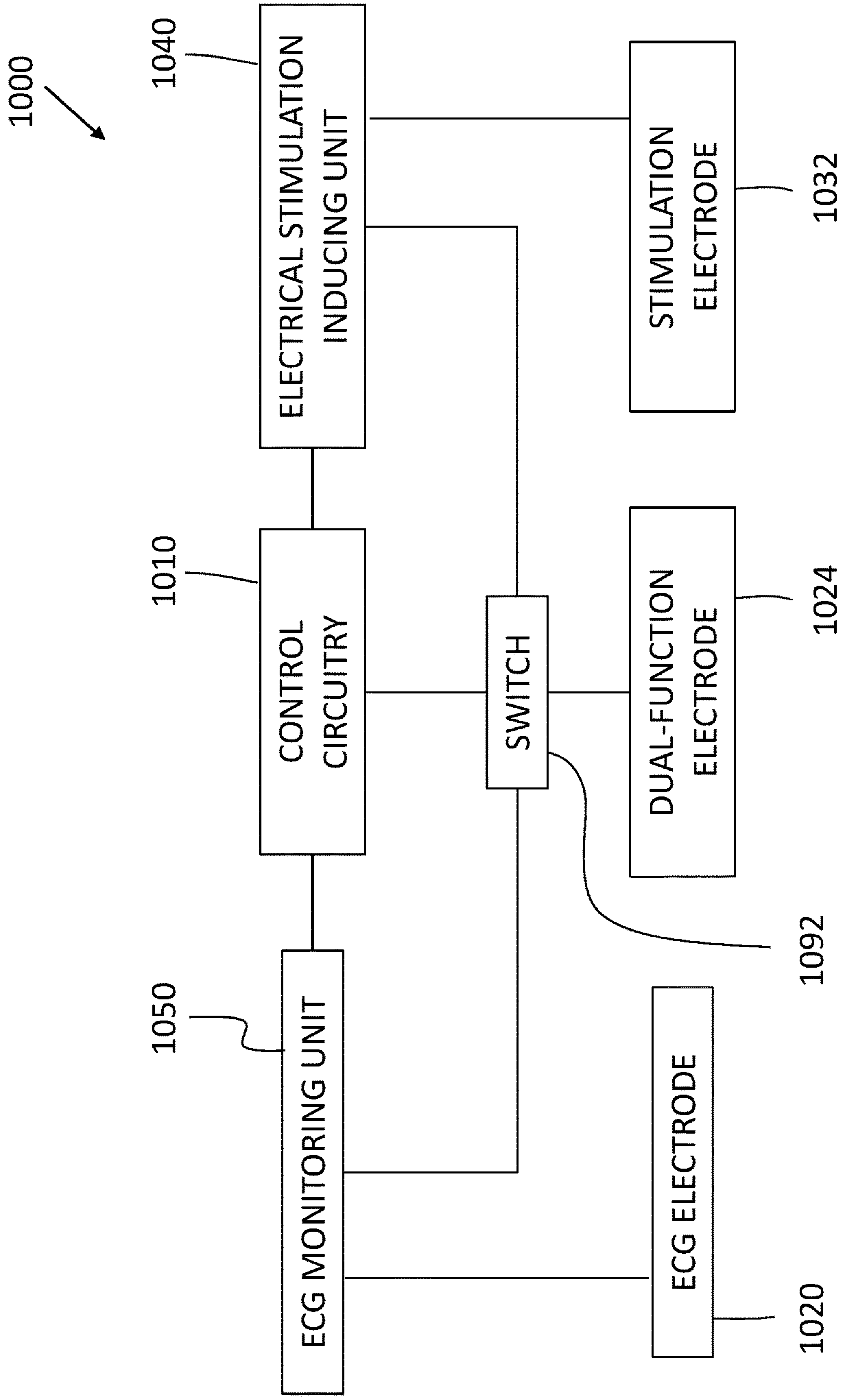
FIG. 10 schematically depicts a block diagram of a monitoring and treatment device, according to some embodiments.

Reference is now made to FIG. 10, which schematically depicts a block diagram of a monitoring and treatment device 1000, according to some embodiments. In some embodiments, device 1000 includes a controller, such as control circuitry 1010, configured to control a heart monitoring unit, such as ECG monitoring unit 1050, and a stimulation inducing unit, such as electrical stimulation inducing unit 1040. In some embodiments, ECG monitoring unit 1050 is connected to a monitoring electrode, such as ECG electrode 1020, and is also connected through a switching element, such as switch 1092, to a dual function electrode 1024. In some embodiments, electrical stimulation inducing unit 1040 is connected to a stimulation electrode 1032, and is also connected through switch 1092, to dual function electrode 1024.

In some embodiments, control circuitry 1010 is also connected to switch 1092 to controllably switch the connection of dual function electrode 1024 to either ECG monitoring unit 1050 or electrical stimulation inducing unit 1040. In some embodiments, control element 1010 is configured to provide an indication/signal to enable/turn-on electrical stimulation inducing unit 1040 and control switch 1092 to connect dual function electrode 1024 to electrical stimulation inducing unit 1040, thereby enabling/initiating a stimulation mode in which electrical stimulation unit 1040 is configured to drive electric current or induce electric potential difference between stimulation electrode 1032 and dual function electrode 1024.

In some embodiments, control circuitry 1010 is further configured to provide an indication/signal to enable/turn-on ECG monitoring unit 1050 and control switch 1092 to connect dual-function electrode 1024 to ECG monitoring unit 1050, thereby enabling/initiating a monitoring mode in which ECG monitoring unit 1050 is configured to obtain an electric (differential-electric) signal from ECG electrode 1020 and dual function electrode 1024.

Figure 11:
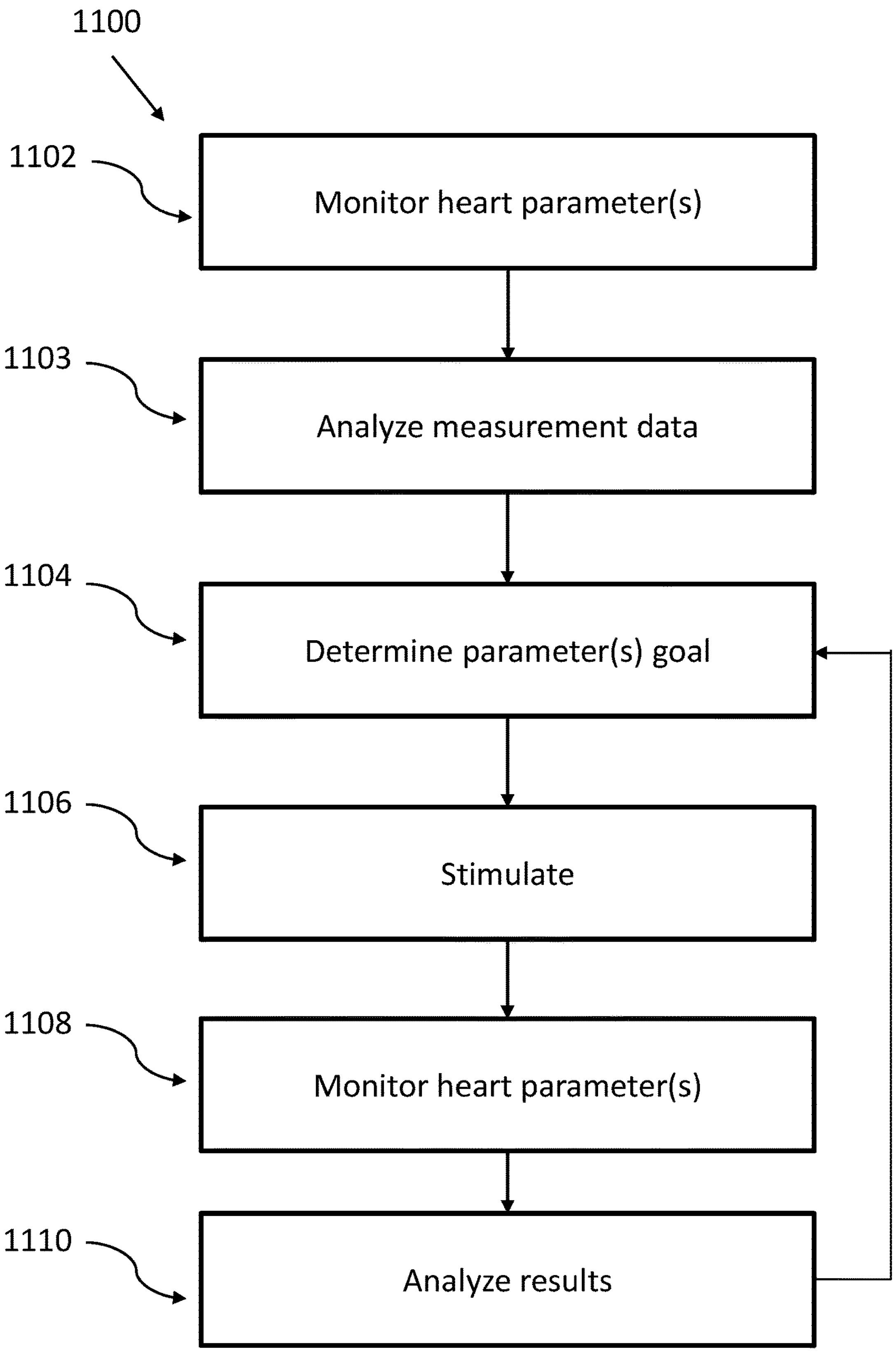
FIG. 11 schematically depicts a method for recursive treatment and monitoring, according to some embodiments.

Reference is now made to FIG. 11, which schematically depicts a method 1100 for recursive treatment and monitoring, according to some embodiments. In some embodiments, method 1100 is initiated by monitoring a heart parameter(s) of the user (step 1102), then analyzing the heart parameter(s) (step 1103) and determining/setting goals/targets to the parameter(s) (step 1104) and providing stimulation (step 1106) based on the determined goals. Then, the heart parameter(s) is monitored once more (step 1108) after the stimulation, and the recently monitored parameter(s) is analyzed (step 1110) in comparison with the determined goals and the previous values of the monitored parameter(s). According to the analysis, new goals may be set, or stimulation parameters may be modified for achieving the goals.

According to some embodiments, a monitoring and treatment device includes/utilizes machine learning algorithms for studying the responses of various parameters to stimulation under certain conditions, and adapting the stimulation conditions to better meet the goals for future treatments/ stimulation-sessions.

According to some embodiments, the stimulation parameters and conditions are modified based on the measurements performed prior to previous stimulation sessions, thus performing a closed-loop stimulation and adjustment cycle for obtaining a desired efficacy. According to some embodiments. The closed loop cycle of the system may include stimulation, measurements, send measurements to an analysis computer, analyze data and adjust stimulation conditions/ parameters accordingly, send back to measurements and stimulation device, and provide a stimulation using the adjusted parameters.

According to some embodiments, a monitoring and treatment device includes an error-correction unit or algorithm for correcting measurement errors in the monitoring unit.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

What is claimed is:

1. A portable module for monitoring of one or more heart parameters, and non-intrusive electrical neuro-stimulation of one or more peripheral nerves, and of a subject, comprising:

a flexible cuff having an inner surface and an outer surface and shaped and sized to be worn, at least in part, around a target body part of the subject such that the inner surface is brought into dermal contact with the target body part, and the outer surface is not in dermal contact with the target body part;

a monitoring electrode, mounted in/on the outer surface of the flexible cuff;

a stimulation electrode and a dual-function electrode, mounted in/on the inner surface of the flexible cuff;

a monitoring unit for monitoring electrical activity;

a stimulation unit for inducing electrical signals; and a control unit;

wherein each of said electrodes is at least partly exposed;

wherein said control unit is configured to enable controllably switching between at least two modes of operation of the portable module:

a first mode, wherein said monitoring unit is functionally associated with said monitoring and dual-function electrodes; and a second mode, wherein said stimulation unit is functionally associated with said stimulation and dual-function electrodes;

wherein the flexible cuff is configured to facilitate simultaneously establishing dermal contact:

(i) between the target body part of the subject and said dual-function electrode, and (ii) between an opposing body part to the target body part and said monitoring electrode, thereby allowing, in the first mode, to obtain heart parameters of the subject by monitoring electrical activity at said dual-function and monitoring electrodes; and wherein the flexible cuff is further configured to facilitate establishing dermal contact between the target body part and both of said dual-function electrode and said stimulation electrode, thereby allowing, in the second mode, to electrically neuro-stimulate at least one peripheral nerve in the target body part, by inducing an electrical signal between said dual-function and stimulation electrodes.

2. The module of claim 1, wherein the one or more heart parameters include heart-rate and/or heart-rate variability (HRV).

3. The module of claim 1, wherein said monitoring unit is configured to perform an electrocardiography (ECG) of the subject.

4. The module of any one of claim 1, wherein the module is configured to be independently held against the target body part.

5. The module of claim 4, wherein the target body part is an inner part of a wrist, an arm, a forearm, a leg or a neck.

6. The module of claim 5, wherein the at least one peripheral nerve is a median nerve in the wrist, arm or forearm.

7. The module of claim 1, wherein said stimulation electrode is a first stimulation electrode and wherein the stimulation signal is a first stimulation signal;

the module further comprising a second stimulation electrode mounted in/on said inner surface such as to be at least partly exposed and such that said dual-function electrode is positioned between said first stimulation electrode and said second stimulation electrode; and wherein the module is further configured to facilitate establishing dermal contact between the target body part and said second stimulation electrode, thereby allowing, in the second mode, to induce a second stimulation signal, between said dual-function electrode and said second stimulation electrode, optionally simultaneously with, or alternately with, the first stimulation signal, thereby electrically neuro-stimulating the at least one peripheral nerve in the target body part.

8. The module of claim 1, wherein said stimulation electrode is a first stimulation electrode and wherein the stimulation signal is a first stimulation signal;

the module further comprising a second stimulation electrode and a third stimulation electrode mounted in/on said inner surface, such as to be at least partly exposed, wherein said first stimulation electrode, said dual-function electrode, said third stimulation electrode, and said second stimulation electrode are substantially respectively linearly ordered; and wherein the module is further configured to facilitate establishing dermal contact between the target body part and said second and third stimulation electrodes, thereby allowing, in the second mode, to induce a second stimulation signal, between said third stimulation electrode and said second stimulation electrode, optionally simultaneously with, or alternately with, the first stimulation signal, thereby electrically neuro-stimulating a second peripheral nerve in the target body part.

9. The module of claim 8, wherein the target body part is an inner part of a wrist and the at least one peripheral nerve is a median nerve in the wrist, and wherein the second peripheral nerve is an ulnar nerve in the wrist, arm or forearm.

10. The module of claim 1, wherein the stimulation signals are characterized by stimulation parameters determined based on the heart parameters obtained in the first mode.

11. The module of claim 10, wherein the stimulation parameters are selected from the group consisting of: frequency, intensity, amplitude, duration, waveform, intermittency, and polarity, of a voltage signal and/or a current signal.

12. The module of claim 1, wherein the module is modular, such as to allow removable attachment to a wearable device including a processing circuitry, and wherein said module and the wearable device are functionally associated.

13. The module of claim 12, further configured to be controllable via a user interface of the wearable device.

14. The module of claim 12, wherein said monitoring electrode is at least partly exposed on an outer surface of said wearable device, and wherein said dual-function and stimulation electrodes are at least partly exposed on an inner surface of the wearable device.

15. The module of claim 1, wherein the flexible cuff is configured to be worn around a limb or a neck of the subject, said flexible cuff having an inner surface and an outer surface;

wherein said monitoring electrode, is at least partly exposed on said outer surface and said dual-function and stimulation electrodes are at least partly exposed on said inner surface; and wherein the target body part is located within the limb or the neck.

16. The module of claim 15, wherein said flexible cuff further comprises a user interface, configured to facilitate control over an operation of said module.

17. The module of claim 16, wherein said user interface comprising a display, configured to provide graphical indications related to the operation of said module; wherein the graphical indications comprise the heart parameters obtained in the first mode and/or the stimulation parameters obtained in the second mode.

18. The module of claim 17, wherein said user interface is configured to display during the second mode an ECG/HR/HRV reading of the subject.

19. A method for operating the module of claim 1, comprising the steps of:

fastening the flexible cuff around a wrist, of the subject, such that the stimulation electrode and the dual-function electrode are in dermal contact with an inner part of the wrist, with the dual-function electrode being located proximately to a median and/or an ulnar nerve in the wrist;

selecting the first mode of operation and bringing an opposing body part into contact with the monitoring electrode;

measuring heart-related activity of the subject by monitoring electrical activity between the monitoring electrode and the dual-function electrode, and determining heart parameters therefrom;

determining stimulation parameters based on the heart parameters; and selecting the second mode of operation, and applying electrical stimulation at the inner part of the wrist by generating a stimulation signal between the stimulation electrode and the dual-function electrode.

20. The method of claim 19, further comprising, subsequently to said step of selecting the second mode of operation, reapplying said steps of selecting the first mode of operation, measuring the heart-related activity, and determining the stimulation parameters, thereby obtaining updated heart parameters, and accordingly adjusting the stimulation parameters.

21. A method for operating the module of claim 1, comprising fastening the flexible cuff around a forearm, an arm, a limb, a leg, or a neck of the subject.

* * * * *